United States Patent [19]
Townsend et al.

[11] Patent Number: 5,874,413
[45] Date of Patent: Feb. 23, 1999

[54] 5'-SUBSTITUTED-RIBOFURANOSYL BENZIMIDAZOLES AS ANTIVIRAL AGENTS

[75] Inventors: Leroy B. Townsend; John C. Drach, both of Ann Arbor, Mich.

[73] Assignee: University of Michigan, Ann Arbor, Mich.

[21] Appl. No.: 698,715

[22] Filed: Aug. 16, 1996

Related U.S. Application Data

[60] Provisional application No. 60/002,542 Aug. 18, 1995.

[51] Int. Cl.[6] ............... C07H 17/02; C07D 235/04; A61K 31/70; A61K 31/415
[52] U.S. Cl. ............... 514/43; 514/394; 548/304.7; 536/28.9
[58] Field of Search ............... 548/304.7; 536/28.9; 514/43, 394

[56] References Cited

U.S. PATENT DOCUMENTS

| | | | |
|---|---|---|---|
| 5,248,672 | 9/1993 | Townsend et al. | 514/43 |
| 5,360,795 | 11/1994 | Townsend et al. | 514/43 |

FOREIGN PATENT DOCUMENTS

| | | |
|---|---|---|
| 0496617 | 7/1992 | European Pat. Off. |
| WO 92/07867 | 5/1992 | WIPO |
| WO 94/08456 | 4/1994 | WIPO |
| WO 96/01833 | 1/1996 | WIPO |
| WO 97/25337 | 7/1997 | WIPO |

OTHER PUBLICATIONS

Classon et al., "New halogenation reagent systems useful for the mild one-step conversion of alcohols into iodides or bromides" *J. Org. Chem.* (1988) vol. 53:6126–6130.

Cory et al., "Use of an aqueous soluble tetrazolium/formazan assay for cell growth assays in culture" *Cancer Comm.* (1991) vol. 3:207–212.

Devivar et al., "Benzimidazole ribonucleosides: Design, synthesis, and antiviral activity of certain 2-(alkylthio)–and 2-(benzylthio)–5, 6–dichloro–1–(β–D–ribofuranosyl)benzimidazoles" *J. Med. Chem.* (1994) vol. 37:2942–2949.

Dobrowolska et al., "Benzimidazole nucleoside analogues as inhibitors of plant (maize seedling) casein kinases" *Biochim. Biophys. Acta* (1991) vol. 1080:221–226.

Egyhazi et al., "Specific inhibition of hnRNA synthesis by 5,6–dichloro–1–β–D–ribofuranosylbenzimidazole. Requirement of a free 3'–hydroxyl group, but not 2'–or 5'–hydroxyls" *Biochim. Biophys. Acta* (1982) vol. 697:213–220.

Goldstein, "Analysis of a single curve with graded responses" *Biostatistics: An Introductory Text*, MacMillan, New York (1964) pp. 156–161.

Hanessian et al. "Design and reactivity of organiz functional groups—2–pyridylsulfonates as nucleofugal esters: Remarkably mild transformations into halides and olefins" *Heterocycles* (1989) vol. 2:1115–1120.

Holy et al. "5'–0–alkyl–5–fluorouridines: Synthesis and biological activity" *Collect. Czech. Chem. Commun.* (1987) vol. 52:1589–1608.

Kanazawa et al., "Studies on d–Ribose derivatives: II.. Preparation of 2,3–Di–O–acetyl–t–deoxy–5–iodo–D–ribofuranosylchloride from 5–0–trityl–D–ribose" *Nippon Kagaku Zasshi*, (1959) vol. 80:200–203.

Kanazawa, "A new synthesis of 9β–(5'methylthio–D–ribofuranosyl)–adenine" *Chem. Abstr.* (1961) vol. 55, Abst. No. 6485.

Kazimierczuk et al., "Preparation and properties of the 5,6–and 4,6(5,7)–dinitro derivatives of benzimidazole and their 1–β–D–ribofuranosides" *NUcleosides and Nucleotides* (1989) vol. 8:1379–1385.

Kazimierczuk et al., "Synthesis of, and conformational studies on, 2–trifluoromethyl substituted benzimidazole ribofuranosides" *Nucleosides and Nucleotides* (1982) vol. 1:275–287.

Kissman et al., "5–deoxy–5–fluoro–D–ribofuranosyl derivatives of certain purines, pyrimidines and 5,6–dimethylbenzimidazole" *J. Chem. Soc.* (1958) vol. 80:5559–5564.

Kissman et al., "The synthesis of certain 5–deoxy–D–ribofuranosylpurines" *J. Am. Chem. Soc.* (1957) vol. 79:5534–5540.

Montgomery et al., "Analogs of 5'–deoxy–5'(methylthio)adenosine" *J. Med. Chem.* (1974) vol. 17:1197–1209.

Perrin et al., *Purification of Laboratory Chemicals*, (1988) 3rd Ed., Pergamon Press, New York. A title page and table of contents are enclosed herewith.

(List continued on next page.)

*Primary Examiner*—Laura L. Stockton
*Attorney, Agent, or Firm*—Morrison & Foerster LLP

[57] ABSTRACT

The present invention relates to polysubstituted benzimidazoles, having the following formula:

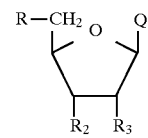

wherein Q is a substituted benzimidazole group attached at the benzimidazole 1-position; R is a halogen of atomic number 9 to 53, inclusive (i.e., —F, —Cl, —Br, or —I); azido (i.e., —$N_3$); or —X—$R_1$, wherein X is a chalcogen of atomic number 8 to 16, inclusive (i.e., —O— or —S—), and $R_1$ may be straight or branched chain alkyl of 1 to 8 carbon atoms; and $R_2$ and $R_3$ may be the same or different and are separately —O—C(=O)$CH_3$ (i.e., —OAc) or hydroxy (i.e., —OH); and pharmaceutically acceptable salts and operative combinations thereof. Also provided by this invention are compositions comprising a polysubstituted benzimidazole as defined above and methods of use thereof.

64 Claims, 5 Drawing Sheets

OTHER PUBLICATIONS

Prichard et al., "A microtiter virus yield reduction assay for the evaluation of antiviral compounds against human cytomegalovirus and herpes simplex virus" *J. Virol. Methods* (1990) vol. 28:101–106.

Prichard et al., "A Three–dimensional model to analyze drug–drug interactions" *Antiviral Res.* (1991) Supplement I Abstract No. 133.

Revankar et al., "The synthesis of 2–chloro–1–(βD–ribofuranosyl) benzimidazole and certain related derivatives" *J. Heterocyclic Chem.* (1968) vol. 5:477–483.

Revankar et al., "The synthesis of 2–chloro–1–βD–ribofuranosyl–5,6–dimethylbenzimidazole and certain related derivatives (1)" *J. Heterocyclic Chem.* (1968) vol. 5:615–620.

Saluja et al. "Synthesis and antiviral activity of certain 2–substituted–5,6–dichlorobenzimidazole acyclic nucleosides" Poster #146, Division of Medicinal Chemistry, 204th American Chemical Society National Meeting, Washington D. C., Aug. 23–28, 1992.

Shipman et al., "Antiviral activity of arabinosyladenine and arabinosylhypoxanthine in herpes simplex virus–infected KB cells: Selective inhibition of viral deoxyribonucleic acid synthesis in synchronized suspension cultures" *Antimicrob. Agents Chemother.* (1976) vol. 9:120–127.

Still et al., "Rapid chromatographic technique for preparative separations with moderate resolution" *J. Org. Chem.* (1978) vol. 43:2923–2925.

Tamm, "Inhibition of influenza and mumps virus multiplication by 4,5–6–(or 5,6,7–) trichloro–1–β–D–ribofuranaosyl–benzimidazole" *Science* (1954) vol. 120:847–848.

Turk et al., "Pyrrolo[2,3–d]pyrimidine nucleosides as inhibitors of human cytomegalovirus" *Antimicro. Agents Chemother.* (1987) vol. 31:544–550.

Verheyden et al., "Halo sugar nucleosides. IV. Synthesis of some 4'5'–unsaturated pyrimidine nucleosides" *J. Org. Chem.* (1974) vol. 39:3573–3579.

Vorbrüggen et al., "Nucleoside synthesis with trimethylsilyl triflate and perchlorate as catalysts" *Chem. Ber.* (1981) vol. 114:1234–1255.

Vorbrüggen et al., "On the mechanism of nucleoside synthesis" *Chem. Ber.* (1981) vol. 114:1256–1268.

Weiss et al., "The reaction of periodate with aminosugars. Anomalous overoxidations of aminofuranosides" *J. Am. Med. Soc.*(1959) vol. 81:4050–4054.

Wotring et al., "Study of the cytotoxicity and metabolism of 4–amino–3–carboxamido–1–(β–D–ribofuranosyl)pyrazolo [3,4–d]pyrimidine using inhibitors of adenosine kinase and adenosine deaminase" *Cancer Res.* (1979) vol. 39:3018–3023.

1

TCRB

2

5'-deoxy-TCRB

# 5,874,413

5'-SUBSTITUTED-RIBOFURANOSYL BENZIMIDAZOLES AS ANTIVIRAL AGENTS

This invention was made with government support under Grant No. UO I -AI31718 from the National Institute of Allergy and Infectious Diseases, National Institutes of Health. The U.S. government has certain rights in this invention.

This application claims the benefit of U.S. provisional application 60/002,542 filed Aug. 18, 1995.

TECHNICAL FIELD

The present invention relates generally to polysubstituted benzimidazole nucleosides and, more particularly, to novel 5'-substituted-ribofuranosyl benzimidazoles, compositions containing same, as well as their use as antiviral agents.

BACKGROUND ART

Benzimidazole nucleosides are particularly attractive as potential antiviral agents because of their ability to avoid some major pathways of bioactive purine (bicyclic) nucleoside inactivation, e.g., deamination by adenosine deaminase and glycosidic bond cleavage by purine nucleoside phosphorylases. However, known benzimidazole nucleosides such as 5,6-dichloro-1-(β-D-ribofuranosyl) benzimidazole (DRB) have demonstrated only marginal levels of activity or generally unacceptable levels of cytotoxicity, or both, thereby greatly diminishing their usefulness in the treatment of viral infections.

A number of benzimidazole nucleosides have been synthesized and tested for their antiviral activity and cytotoxicity in an effort to identify a compound with superior anti-human cytomegalovirus (HCMV) activity to ganciclovir and foscarnet. Antiviral activity of polysubstituted benzimidazoles such as 5,6-dichloro-1 -(β-D-ribofuranosyl) benzimidazole (DRB) and some closely related derivatives have been previously described (I. Tamm, *Science* (1954) Vol. 120:847–848). Their activity against specific viruses, such as RNA rhinovirus and DNA herpes simplex virus type 1 and type 2, also has been reported.

Several of the ribofuranosyl benzimidazole analogs, including 2,5,6-trichloro-1 -(β-D-ribofuranosyl) benzimidazole (TCRB) have shown very potent activity against HCMV and low cellular toxicity at concentrations inhibiting viral growth. Structural activity relationships of TCRB and heterocycle and carbohydrate modified derivatives have been reported. (See, Revankar, G. R. and Townsend, L. B. (1968) *J. Heterocyclic Chem.* Vol. 5:477–483; Townsend, L. B. and Drach, J. C., Fifth International Conference on Antiviral Research Vancouver, British Columbia, March 1992; Revankar, G. R. and Townsend, L. B. (1968) *J. Heterocyclic Chem.* Vol. 5:615–620; Zou, R. et al. "Design, synthesis and antiviral evaluation of some TCRB analogs modified on the benzene moiety," Poster #142, Division of Medicinal Chemistry, 204th American Chemical Society National Meeting, Washington, D. C., Aug. 23–28, 1992; and Saluja, S. et al. "Synthesis and antiviral activity of certain 2-substituted-5,6-dichlorobenzimidazole acyclic nucleosides," Poster #146, Division of Medicinal Chemistry, 204th American Chemical Society National Meeting, Washington, D. C., Aug. 23–28, 1992.) A number of substituted benzimidazoles have also been described in U.S. Pat. No. 5,248,672 and U.S. Pat. No. 5,360,795. These disclosures, however, do not disclose the structure or synthesis of the compounds which are the subject of this invention.

Some modifications of the heterocycle have given analogs that are significantly more active than TCRB. However, most of these analogs are also more cytotoxic than TCRB, resulting in compounds with a little improved therapeutic index. Attempts to modify the carbohydrate moiety, by replacing the ribose with arabinose, xylose or acyclic analogues have given compounds less active than TCRB. Somewhat surprisingly a 5'-deoxy-β-D-ribofuranosyl derivative of TCRB, 2,5,6-trichloro-1-(5'-deoxy-β-D-ribofuranosyl) benzimidazole, was shown to be about 10 times more active than TCRB and have a better therapeutic index than TCRB. However, no other 5'-modified derivatives, other than 2-bromo and 2-chloro analogs disclosed in U.S. Pat. No. 5,360,795, have been reported to date.

DISCLOSURE OF INVENTION

The present invention relates to 5'-substituted-ribofuranosyl benzimidazoles wherein a 5'-substituted-ribofuranosyl group is attached at the 1-position of a substituted benzimidazole group, Q, said 5'-substituted-ribofuranosyl benzimidazole having the following general formula:

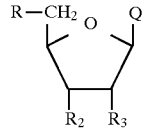

wherein Q is a substituted benzimidazole group; R is a halogen of atomic number 9 to 53, inclusive (i.e., —F, —Cl, —Br, or —I); azido (i.e., —$N_3$); or —X—$R_1$, wherein X is a chalcogen of atomic number 8 to 16, inclusive (i.e., —O— or —S—), and $R_1$ may be straight or branched chain alkyl of 1 to 8 carbon atoms; and $R_2$ and $R_3$ may be the same or different and are separately —O—C(=O)$CH_3$ (i.e., —OAc) or hydroxy (i.e., —OH); and pharmaceutically acceptable salts and operative combinations thereof.

Preferred embodiments of the present invention include 5'-substituted-ribofuranosyl benzimidazoles having the following formula, wherein R, $R_2$, and $R_3$ are as defined above:

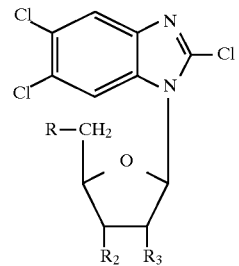

Also provided by this invention are compositions comprising a polysubstituted benzimidazole as defined above and a carrier, such as a pharmaceutically acceptable carrier.

Further provided are methods of inhibiting HCMV reproduction and proliferation in a cell infected with HCMV comprising contacting the cell with an effective amount of a polysubstituted benzimidazole as described herein.

MODES FOR CARRYING OUT THE INVENTION

Figure 1:
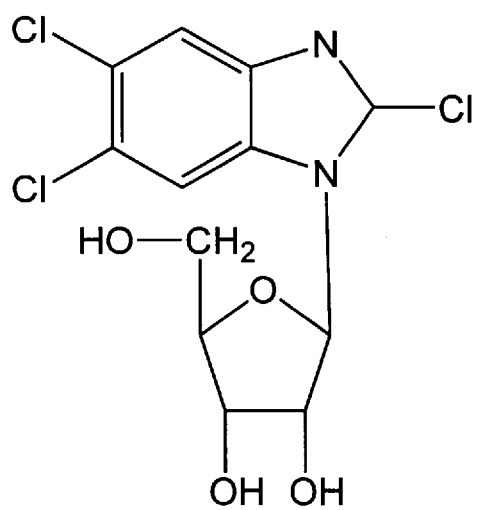
FIG. 1 shows the structures of 2,5,6-trichloro-1-(β-D-ribofuranosyl) benzimidazole (TCRB) and 2,5,6-trichloro-1-(5'-deoxy-β-D-ribofuranosyl)benzimidazole.
Figure 1:
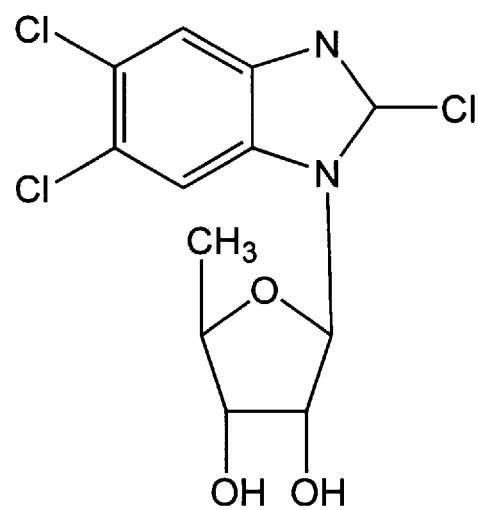

The present invention relates to 5'-substituted-ribofuranosyl benzimidazoles wherein a specific 5'-substituted-ribofuranosyl group is attached at the 1-position of a substituted benzimidazole group, Q, said 5'-substituted-ribofuranosyl benzimidazole having the following general formula:

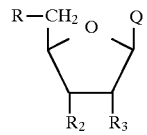

wherein Q is a substituted benzimidazole group; R is a halogen of atomic number 9 to 53, inclusive (i.e., —F, —Cl, —Br, or —I); azido (i.e., —N$_3$); or —X—R$_1$, wherein X is a chalcogen of atomic number 8 to 16, inclusive (i.e., —O— or —S—), and R$_1$ may be straight or branched chain alkyl of 1 to 8 carbon atoms; and R$_2$ and R$_3$ may be the same or different and are separately —O—C(=O)CH$_3$ (i.e., —OAc) or hydroxy (i.e., —OH); and pharmaceutically acceptable salts and operative combinations thereof.

Examples of substituted benzimidazole groups include halobenzimidazoles, such as halo-, dihalo-, trihalo-, tetrahalo-, and pentahalobenzimidazoles, including but not limited to, 2,5,6-trihalobenzimidazole (e.g., 2,5,6-trichlorobenzimidazole, 2-bromo-5,6-dichlorobenzimidazole), 2,4,6-trihalobenzimidazole (e.g., 2,4,6-trichlorobenzimidazole, 2-bromo-4,6-dichlorobenzimidazole), 2,4,5,6-tetrahalobenzimidazole (e.g., 2,4,5,6-tetrachlorobenzimidazole, 2-bromo-4,5,6-trichlorobenzimidazole). Other examples of substituted benzimidazole groups include 2-substituted-4,5-dihalobenzimidazoles (e.g., 2-amino-4,5-dichlorobenzimidazole, 2-isopropylamino-4,5-dichlorobenzimidazole, 2-methoxy-4,5-dichlorobenzimidazole, 2-trifluoromethyl-4,5-dichlorobenzimidazole). A number of substituted benzimidazoles compounds, and methods for their preparation, are known in the art. (See, for example, U.S. Pat. No. 5,248,672, which is incorporated herein by reference.) In a preferred embodiment of the present invention, the substituted benzimidazole group is a 2,5,6-trichlorobenzimidazole group.

Examples of straight chain alkyls of 1 to 8 carbon atoms include methyl (i.e., —CH$_3$), ethyl (i.e., —CH$_2$CH$_3$), n-propyl (i.e., —CH$_2$CH$_2$CH$_3$), n-butyl (i.e., —CH$_2$CH$_2$CH$_2$CH$_3$), and n-hexyl (i.e., —CH$_2$CH$_2$CH$_2$CH$_2$CH$_2$CH$_3$).

Preferred embodiments of the present invention include 5'-substituted-ribofuranosyl benzimidazoles having the following formula, wherein R, R$_2$, and R$_3$ are as defined above:

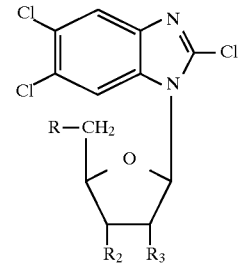

Throughout this application the specifically disclosed and claimed compounds are identified by structure, name or by numerical designations. The compounds of this invention include, but are not limited to, the following, as well as their α and L analogs:

2,5,6-trichloro-1-(5'-O-methyl-β-D-ribofuranosyl) benzimidazole (8a);

2,5,6-trichloro-1-(2',3'-di-O-acetyl-5'-O-methyl-β-D-ribofuranosyl)benzimidazole (7a);

2,5,6-trichloro-1-(3'-O-acetyl-5'-O-methyl-β-D-ribofuranosyl)benzimidazole;

2,5,6-trichloro-1-(2'-O-acetyl-5'-O-methyl-β-D-ribofuranosyl)benzimidazole;

2,5,6-trichloro-1-(5'-O-ethyl-β-D-ribofuranosyl) benzimidazole (8b);

2,5,6-trichloro-1-(2',3'-di-O-acetyl-5'-O-ethyl-β-D-ribofuranosyl)benzimidazole (7b);

2,5,6-trichloro-1-(3'-O-acetyl-5'-O-ethyl-β-D-ribofuranosyl)benzimidazole;

2,5,6-trichloro-1-(2'-O-acetyl-5'-O-ethyl-β-D-ribofuranosyl)benzimidazole;

2,5,6-trichloro-1-(5'-O-butyl-β-D-ribofuranosyl) benzimidazole (8c);

2,5,6-trichloro-1-(2',3'-di-O-acetyl-5'-O-butyl-β-D-ribofuranosyl)benzimidazole (7c);

2,5,6-trichloro-1-(3'-O-acetyl-5'-O-butyl-β-D-ribofuranosyl)benzimidazole;

2,5,6-trichloro-1-(2'-O-acetyl-5'-O-butyl-β-D-ribofuranosyl)benzimidazole;

2,5,6-trichloro-1-(5'-O-hexyl-β-D-ribofuranosyl) benzimidazole (8d);

2,5,6-trichloro-1-(2',3'-di-O-acetyl-5'-O-hexyl-β-D-ribofuranosyl)benzimidazole (7d);

2,5,6-trichloro-1-(3'-O-acetyl-5'-O-hexyl-β-D-ribofuranosyl)benzimidazole;

2,5,6-trichloro-1-(2'-O-acetyl-5'-O-hexyl-β-D-ribofuranosyl)benzimidazole;

2,5,6-trichloro-1-(5'-deoxy-5'-fluoro-β-D-ribofuranosyl) benzimidazole (13a)

2,5,6-trichloro-1-(2',3'-di-O-acetyl-5'-deoxy-5'-fluoro-β-D-ribofuranosyl)benzimidazole (12a);

2,5,6-trichloro-1-(3'-O-acetyl-5'-deoxy-5'-fluoro-β-D-ribofuranosyl)benzimidazole;

2,5,6-trichloro-1-(2'-O-acetyl-5'-deoxy-5'-fluoro-β-D-ribofuranosyl)benzimidazole;

2,5,6-trichloro-1-(5'-deoxy-5'-chloro-β-D-ribofuranosyl) benzimidazole (13b);

2,5,6-trichloro-1-(2',3'-di-O-acetyl-5'-deoxy-5'-chloro-β-D-ribofuranosyl)benzimidazole (12b);

2,5,6-trichloro-1-(3'-O-acetyl-5'-deoxy-5'-chloro-β-D-ribofuranosyl)benzimidazole;

2,5,6-trichloro-1-(2'-O-acetyl-5'-deoxy-5'-chloro-β-D-ribofuranosyl)benzimidazole;

2,5,6-trichloro-1-(5'-deoxy-5'-bromo-β-D-ribofuranosyl) benzimidazole (13c);

2,5,6-trichloro-1-(2',3'-di-O-acetyl-5'-deoxy-5'-bromo-β-D-ribofuranosyl)benzimidazole (12c);

2,5,6-trichloro-1-(3'-O-acetyl-5'-deoxy-5'-bromo-β-D-ribofuranosyl)benzimidazole;

2,5,6-trichloro-1-(2'-O-acetyl-5'-deoxy-5'-bromo-β-D-ribofuranosyl)benzimidazole;

2,5,6-trichloro-1-(5'-deoxy-5'-iodo-β-D-ribofuranosyl) benzimidazole (13d);

2,5,6-trichloro-1-(2',3'-di-O-acetyl-5'-deoxy-5'-iodo-β-D-ribofuranosyl)benzimidazole (12d);

2,5,6-trichloro-1-(3'-O-acetyl-5'-deoxy-5'-iodo-β-D-ribofuranosyl)benzimidazole;

2,5,6-trichloro-1-(2'-O-acetyl-5'-deoxy-5'-iodo-β-D-ribofuranosyl)benzimidazole;

2,5,6-trichloro-1-(5'-deoxy-5'-azido-β-D-ribofuranosyl) benzimidazole (17a);

2,5,6-trichloro-1-(2',3'-di-O-acetyl-5'-deoxy-5'-azido-p-D-ribofuranosyl)benzimidazole (16a);

2,5,6-trichloro-1-(3'-O-acetyl-5'-deoxy-5'-azido-β-D-ribofuranosyl)benzimidazole;

2,5,6-trichloro-1-(2'-O-acetyl-5'-deoxy-5'-azido-β-D-ribofuranosyl)benzimidazole;

2,5,6-trichloro-1-(5'-deoxy-5'-methylthio-β-D-ribofuranosyl)benzimidazole (17b);

2,5,6-trichloro-1-(2',3'-di-O-acetyl-5'-deoxy-5'-methylthio-β-D-ribofuranosyl) benzimidazole (16b);

2,5,6-trichloro-1-(3'-O-acetyl-5'-deoxy-5'-methylthio-β-D-ribofuranosyl)benzimidazole;

2,5,6-trichloro-1-(2'-O-acetyl-5'-deoxy-5'-methylthio-β-D-ribofuranosyl)benzimidazole;

Also preferred are compounds wherein $R_2$ and $R_3$ are each hydroxyl and wherein R is any of the halogens: fluorine (designated compound 13a); chlorine (designated compound 13b); bromine (designated compound 13c); or iodine (compound 13d), or wherein R is any of methoxy (compound 8a), ethoxy (compound 8b), n-butoxy (compound 8c), n-hexoxy (compound 8d), azido (compound 17a) or methylthio (compound 17b).

Also preferred are compounds wherein $R_2$ and $R_3$ are each acetyl, and wherein R is any of the halogens: fluorine (designated compound 12a); chlorine (designated compound 12b); bromine (designated compound 12c); or iodine (compound 12d), or R is methoxy (compound 7a), ethoxy (compound 7b), n-butoxy (compound 7c), n-hexoxy (compound 7d), azido (compound 16a) or methylthio (compound 16b).

Additionally, throughout this application, the disclosed and claimed ribofuranose compounds are identified by structure, name or by numerical designations. The ribofuranose compounds of this invention include, but are not limited to the following, as well as their α, β, and L analogs:

1-O-methyl-2,3-O-isopropylidene-5-O-methyl-D-ribofuranose (5a);

1-O-methyl-2,3-O-isopropylidene-5-O-ethyl-D-ribofuranose (5b);

1-O-methyl-2,3-O-isopropylidene-5-O-butyl-D-ribofuranose (5c);

1-O-methyl-2,3-O-isopropylidene-5-O-hexyl-D-ribofuranose (5d);

1,2,3-tri-O-acetyl-5-O-methyl-D-ribofuranose (6a);

1,2,3-tri-O-acetyl-5-O-ethyl-D-ribofuranose (6b);

1,2,3-tri-O-acetyl-5-O-butyl-D-ribofuranose (6c);

1,2,3-tri-O-acetyl-5-O-hexyl-D-ribofuranose (6d);

1-O-methyl-2,3-O-isopropylidene-5-deoxy-5-fluoro-D-ribofuranose (10a);

1-O-methyl-2,3-O-isopropylidene-5-deoxy-5-chloro-D-ribofuranose (10b);

1-O-methyl-2,3-O-isopropylidene-5-deoxy-5-bromo-D-ribofuranose (10c);

1-O-methyl-2,3-O-isopropylidene-5-deoxy-5-iodo-D-ribofuranose (10d);

1,2,3-tri-O-acetyl-5-deoxy-5-fluoro-β-D-ribofuranose (11a);

1,2,3-tri-O-acetyl-5-deoxy-5-chloro-β-D-ribofuranose (11b);

1,2,3-tri-O-acetyl-5-deoxy-5-bromo-β-D-ribofuranose (11c);

1,2,3-tri-O-acetyl-5-deoxy-5-iodo-β-D-ribofuranose (11d);

1-O-methyl-2,3-O-isopropylidene-5-deoxy-5-azido-D-ribofuranose (14a);

1-O-methyl-2,3-O-isopropylidene-5-deoxy-5-methylthio-D-ribofuranose (14b);

1,2,3-tri-O-acetyl-5-deoxy-5-azido-β-D-ribofuranose (15a); and 1,2,3-tri-O-acetyl-5-deoxy-5-methylthio-β-D-ribofuranose (15b).

The compounds of this invention are useful in the methods provided below or are useful as intermediates for the manufacture of these compounds. It also should be understood, even though not always explicitly stated, that reference to any of the above compounds is to include pharmaceutically acceptable salts and operative combinations thereof.

As shown in the experimental section below, the compounds of this invention are potent antiviral drugs, and are particularly effective against HCMV, and as such, when combined with carriers, provide compositions for inhibiting viral reproduction and proliferation in vitro, ex vivo or in vivo. For example, the compounds can be combined with various liquid phase carriers, such as sterile or aqueous solutions, pharmaceutically acceptable carriers as defined below.

The compounds of this invention can be combined with other antiviral drugs to provide an operative combination. "Operative combination" is intended to include any chemically compatible combination of a compound of this inventive group with other compounds of the inventive group or other compounds outside the inventive group, as long as the combination does not eliminate the antiviral activity of the compound of this inventive group.

This invention also provides a method of reducing or inhibiting a suitable viral reproduction and proliferation in a virally infected cell or population of cells by contacting the cell or population with an effective amount of a compound of this invention and under suitable conditions, such that viral reproduction and proliferation is inhibited. One of skill in the art can easily determine when viral reproduction and proliferation has been reduced or inhibited by noting a reduction in viral titer or an increase of survival of the infected cells as compared to untreated, infected cells. Methods of assaying viral titer are well known to those of skill in the art and are exemplified below. It should be readily understood that by inhibiting and reducing viral replication and proliferation, viral infectivity also is inhibited and reduced and the cells are suitably treated for viral infection.

For the purposes of this invention, a "cell" is intended to include, but not be limited to a mammalian cell, e.g., a mouse cell, a rat cell, a woodchuck cell, a simian cell, or a human cell. Viruses which are effectively treated by the compounds, compositions and methods of this invention include DNA and RNA virus, such as HCMV.

Effective amounts are easily determined by those of skill in the art and will vary with the cell, virus being effected and the purpose of the treatment. For example, when utilizing the drug in cell culture, it is important that the amount of drug not be cytotoxic to the cells.

"Suitable conditions" include in vitro, ex vivo or in vivo. When the method is practiced in vitro, contacting may be effected by incubating the cells with an effective antiviral amount of the compound, effective to inhibit viral reproduction and proliferation in the cell or culture of cells. The compound can be added directly to the culture media or combined with a carrier prior to addition to the cells. In vitro, the method is particularly useful for inhibiting viral reproduction, proliferation and therefore infection in laboratory cell cultures. Ex vivo, the compounds are useful to inhibit viral reproduction and proliferation in blood and plasma prior to reintroduction into a patient.

The use of the compounds and methods in vitro also provides a powerful bioassay to screen for novel drugs or compounds which provide similar or enhanced antiviral activity. Using the methods set forth below, the drug to be tested is assayed under the same conditions as a compound of this invention. Antiviral and cytotoxicity of the test drug can then be compared to a compound of this inventive group.

Although the compounds are shown below to be particularly effective against HCMV, one of skill in the art can easily determine other virus effectively treated with the compounds of this invention by use of methods described below and others well known to those of skill in the art. Other viruses suitable treated and within the scope of the present invention include, but are not limited to: varicella-zoster virus, Epstein-Barr virus, human immunodeficiency virus (HIV) and hepatitis viruses.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

The compositions also can be administered to subjects or individuals susceptible to or at risk of a viral infection, such as HCMV infection. Thus, this invention also provides a prophylactic method of inhibiting viral replication, proliferation and/or viral infection in a subject by administering to a subject an prophylactically effective amount of the compound or composition under suitable conditions such that viral replication, proliferation or infection is inhibited. A "prophylactically effective amount" is an amount which inhibits viral infection, reproduction and proliferation in a subject challenged with the virus without toxicity to the cells and subject being treated.

It should be understood that by preventing or inhibiting viral proliferation, infection and replication in a subject or individual, the compositions and methods of this invention also provide methods for treating, preventing or ameliorating the symptoms or disorders associated with the viral infection, such as inclusion disease, blindness, mononucleosis (HCMV); chickenpox, shingles (varicella-zoster virus); infectious mononucleosis, glandular fever, and Burkittis lymphoma (Epstein-Barr virus); and hepatitis (hepatitis viruses). Thus, this invention also provides methods of ameliorating or treating disorders or symptoms associated with viral infection, e.g., HCMV infection, by administering to the subject an effective amount of a compound of this invention under suitable conditions such that the disorder or symptom is ameliorated or treated.

Administration in vivo can be effected in one dose, continuously or intermittently throughout the course of treatment. Methods of determining the most effective means and dosage of administration are well known to those of skill in the art and will vary with the composition used for therapy, the target virus, the purpose of the therapy, the target cell being treated, and the subject being treated. Single or multiple administrations can be carried out with the dose level and pattern being selected by the treating physician. Suitable dosage formulations and methods of administering the compounds can be found below.

The polysubstituted benzimidazoles of the present invention all exhibit antiviral activity against HCMV, many with acceptable cytotoxicity. It will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g. in immunocompromised patients, such as bone marrow and organ transplant patients as well as patients harboring HIV who are particularly susceptible to HCMV infection.

The compounds and compositions of the present invention can be used in the manufacture of medicaments and in antiviral treatment of humans and other animals by administration in accordance with conventional procedures, such as an active ingredient in pharmaceutical compositions. The compounds of the invention can be provided as pharmaceutically acceptable formulations and/or "prodrugs," including but not limited to esters, especially carboxylic acid esters (preferably $C_1$ to $C_{20}$), such as 5'-acetyl and 2',3',5'-triacetyl prodrugs and pharmaceutical salts such as thiolate, citrate and acetate salts.

The pharmaceutical compositions can be administered topically, orally, intranasally, parenterally or by inhalation therapy, and may take the form of tablets, lozenges, granules, capsules, pills, ampoules, suppositories or aerosol form. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradernal) and pulmonary. It will also be appreciated that the preferred route will vary with the condition and age of the recipient, the virus being treated and the nature of the infection.

In general, a suitable dose for each of the above-named viral infections, e.g., HCMV, is in the range of about 0.1 to about 250 mg per kilogram body weight of the recipient per day, preferably in the range of about 1 to about 100 mg per kilogram body weight per day and most preferably in the range of about 5 to about 20 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 2 $\mu$M to about 100 $\mu$M, preferably about 5 $\mu$M to about 70 $\mu$M, most preferably about 1 to about 50 $\mu$M. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient.

While it is possible for the active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Compounds of the formula of the present invention may also be presented for the use in the form of veterinary formulations, which may be prepared, for example, by methods that are conventional in the art.

Synthesis

The precursor benzimidazole, TCRB and its synthesis is known in the art and is described in U.S. Pat. No. 5,248,672, incorporated herein by reference. To prepare the desired 5'-O-alkylated nucleosides of this invention, the usual synthetic approach, where the pre-formed nucleoside (i.e., TCRB, compound 1) is substituted selectively at the 5'-position with a functional group (i.e., tosyl or mesyl ester) which then is displaced with an appropriate nucleophile, cannot be used because of the lability of the chlorine in the 2-position of the heterocyclic moiety. Thus, a different scheme was devised for their preparation. 1-O-Methyl-2,3-O-isopropylidene-5-O-alkyl-D-ribofuranose derivatives (5a–d) were synthesized from ribose (3) by the conventional method and as described in Holy, A., et al. (1987) Collect. Czech. Chem. Commun. Vol. 52:1589–1608, also incorporated herein by reference. Compounds 5a-d were subsequently converted into 1,2,3-tri-O-acetyl-5-O-alkyl-D-ribofuranose derivatives (6a–d) by removing the isopropylidene and methoxy groups in dilute hydrochloric acid followed by acetylation using acetic anhydride in pyridine. Compounds (6a–d) were isolated in good yields as an anomeric mixture, containing 5–10 % of the α-anomer. (Anomeric assignment is based on the assumption that the 1'-H for the α-anomer appears further downfield (signal appears at 6.3 ppm) than the signal for the 1'-H in the β-anomer (signal appears at 6.0 ppm.) Even though the anomeric mixture was used for subsequent steps, the β-anomers could be separated by flash column chromatography for analytical purposes. This two step procedure for synthesis of compounds (6a–d) is shorter than the four step procedure as described in Holy, A. et al. (1987) supra, used to make the corresponding 1-O-acetyl-2,3-di-O-benzoyl-D-ribofuranose derivatives. To obtain the 2,5,6-trichloro-1-(2', 3'-di-O-benzoyl-5'-O-alkyl-β-D-ribofuranosyl) benzimidazoles (7a–d), compounds (6a–d) were coupled with 2,5,6-trichlorobenzimidazole under modified Vorbruggen conditions. The heterocycle is first silylated using bis(trimethylsilyl)acetamide (BSA) using the well known method of Vorbruggen and described in Vorbruggen, H. and Hofle, G. (1981) Chem. Ber. Vol. 114:1256–1268 (incorporated herein by reference) and subsequently condensed with the sugar derivatives using trimethylsilyltrifluoro-methanesulfonate (TMSOTf) (Aldrich Chemical Company) as a Lewis catalyst using the method known in the art and described in Vorbruggen, H. et al., (1981) Chem. Ber. Vol. 114:1234–1255 (incorporated herein by reference). Finally the protected nucleosides 7a–d were deprotected using anhydrous carbonate in aqueous ethanol to give the target compounds, 2,5,6-trichloro- 1-(5'-O-alkyl-β-D-ribofuranosyl) benzimidazoles (8a–d), in good yields (See FIG. 2).

Two complementary methods could be used for the preparation of 2,5,6-trichloro-1-(5'-deoxy-5'-halo-p-D-ribofuranosyl)benzimidazoles (13a–d). The first scheme requires preparation of the appropriate 1,2,3-tri-O-acetyl-5-deoxy-5-halo-β-D-ribofuranose which could be coupled to 2,5,6-trichlorobenzimidazole under modified Vorbruggen conditions. The second scheme requires direct substitution of a 5'-OH group in 2,5,6-trichloro-1-(2',3'-O-isopropylidene-β-D-ribofuranosyl)benzimidazole with a halogen.

Both methods were investigated for the synthesis of 2,5,6-trichloro-1-(5-deoxy-5-chloro-β-D-ribofuranosyl) benzimidazole (13b) (See FIGS. 3 and 5). 1-O-Methyl-2,3-O-isopropylidene-5-deoxy-5-chloro-β-D-ribofuranose (10b) was synthesized, by methods well known to those of skill in the art and as described in Hanessian, S. et al. (1989) *Heterocycles* Vol. 2:1115–1120 (incorporated herein by reference) from 1-O-methyl-2,3-O-isopropylidene ribofuranose (4). Subsequent removal of the isopropylidene and 1'-methoxy groups under acidic conditions followed by acetylation afforded a 1:10 mixture of the α and β anomers of 1,2,3-tri-O-acetyl-5-deoxy-5-chloro-D-ribofuranose (11b) as determined by $^1$H-NMR of the crude reaction mixture. The pure β-anomer could be crystallized out of the reaction mixture without prior chromatographic purification and was used for subsequent reactions. Compound 11b was then coupled with 2,5,6-trichlorobenzimidazole under modified Vorbruggen conditions to give 2,5,6-trichloro-1-(2',3'-di-O-acetyl-5'-deoxy-5'-chloro-β-D-ribofuranosyl) benzimidazole (12b). Deprotection of 12b afforded 2,5,6-trichloro-1-(5'-deoxy-5'-chloro-β-D-ribofuranosyl) benzimidazole (13b).

Figure 5:
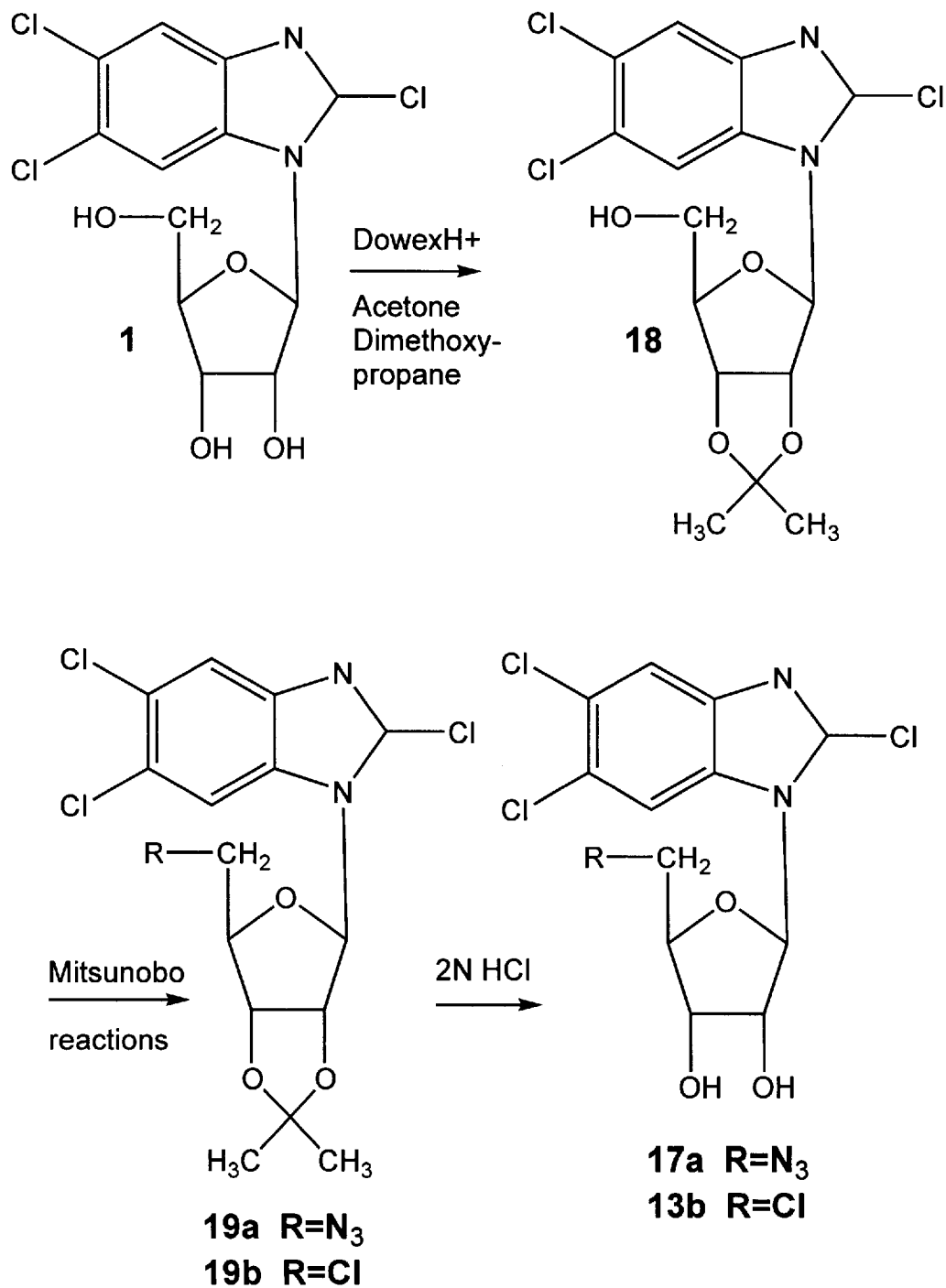
FIG. 5 also is a schematic of the syntheses of a number of 2,5,6-trichloro- 1-(5'-deoxy-5'-chloro-β-D-ribofuranosyl) benzimidazoles and 2,5,6-trichloro- 1 -(5'-deoxy-5'-azido-β-D-ribofuranosyl)benzimidazoles (Scheme 5).

Compound 13b also was synthesized from compound 1 (see FIG. 5). TCRB (1) was treated with acetone, 2,2-dimethoxypropane and Dowex-50H+ to give the 2,3-O-isopropylidene derivative (compound 18). Compound 18 was chlorinated using N-chlorosuccinimide and triphenylphosphine in $CCl_4$ to give 2,5,6-trichloro- 1-(2',3'-O-isopropylidene-5'-deoxy-5'-chloro-β-D-ribofuranosyl) benzimidazole (19b). A tedious chromatographic separation was needed to separate the nucleoside 19b from triphenylphosphine oxide. The isopropylidene group could then be removed under acidic conditions to give compound 13b.

The other 2,5,6-trichloro-1-(5'-deoxy-5'-halo-β-D-ribofuranosyl) benzimidazoles derivatives 13a, 13c and 13d were synthesized from the 1,2,3-tri-O-acetyl-5-deoxy-5-halo-ribofuranoses 11a, 11c and 11d. This possibility gave this synthetic route more versatility. These 5'-substituted ribofuranoses may then be coupled to a benzimidazole, such as 2,5,6-trichlorobenzimidazole as exemplified herein, or other benzimidazoles, as described in detail above. This approach also gives the acetylated nucleosides, which have been shown to be almost equally active to the unprotected derivatives (vide infra). This is in contrast to the isopropylidene derivatives which are less active than the corresponding deprotected nucleoside. Finally this approach uses less of the expensive 2,5,6-trichlorobenzimidazole, which is coupled in high yield to the pre-formed carbohydrate derivative at the end of the synthesis.

1-O-Methyl-2,3-O-isopropylidene-5-deoxy-5-fluoro-D-ribofuranose (10a) was synthesized by well known procedures and as described in Kisman, H. M. and Weiss, M. J. (1958) *J. Chem. Soc.* Vol. 80:5559–5564; 1-O-methyl-2,3-O-isopropylidene-5-deoxy-5-bromo-D-ribofuranose (10c) was synthesized by well known procedures and as described in Classon, B. and Liu, Z. (1988) *J. Org. Chem.* Vol. 53:6126–6130; and 1-O-methyl-2,3-O-isopropylidene-5-deoxy-5-iodo-D-ribofuranose (10d) was synthesized by well known procedures and as described in Kissman, H. M. and Baker, B. R. (1957) *J. Am. Chem. Soc.* Vol. 79:5534–5540, all incorporated herein by reference. These compounds (10a, 10c and 10d) were deprotected and acetylated to give 1,2,3-tri-O-acetyl-5-deoxy-5-fluoro-β-D-ribofuranose (11a) (See, Hanessian, S. et al. (1989) *Heterocycles* Vol. 2:1115–1120), 1,2,3-tri-O-acetyl-5-deoxy-5-bromo-β-D-ribofuranose (11c) and 1,2,3-tri-O-acetyl-5-deoxy-5-iodo-β-D-ribofuranose (11d) (See Kanazawa, T. and Sato, T., (1959) *Nippon Kagaku Zasshi*, Vol. 80:200–203 and Chem. Abstr. (1961) Vol. 55, Abst. No. 6485). In all cases was the β-anomer obtained. The crude reaction mixtures contains a 1:10 ratio of the α and β-anomers as determined by $^1$H-NMR. Anomeric assignment is based on the assumption that the 1'-H signal for the α-anomer (signal at 6.3 ppm)) appears further downfield than the signal for the 1'-H in the β-anomer (signal at 6.0 ppm) crystallized out of the reaction mixtures without prior chromatographic purification. These derivatives (11a, 11c, 11d) were subsequently condensed with the 2,5,6-trichlorobenzimidazole as described to give the 2,5,6-trichloro-1-(2',3'-di-O-acetyl-5'-deoxy-5'-halo-β-D-ribofuranosyl) benzimidazoles (12a, 12c and 12d). Compounds 12a and 12c were deprotected as before to afford the 2,5,6-trichloro-1-(5'-deoxy-5'-halo-β-D-ribofuranosyl) benzimidazoles 13a and 13c. Attempts to deprotect 12d to obtain 13d have given several products in low yield. The iodo group, which is a good leaving group, may be eliminated upon treatment of 12d with a base to give a 4',5'-unsaturated nucleoside (See Verheyden, J. P. H. and Moffatt, J. G. (1974) *J. Org. Chem.* Vol. 39:3573–3579).

Thiols have been shown to displace the 2-chlorine in the 2,5,6-trichlorobenzimidazole nucleosides (See, Devivar R. D., "Design and Synthesis of 2-Substituted Analogs of 2,5,6-Trichloro-1-(β-D-ribofuranosyl)benzimidazole and Related Imidazo[4,5-β]pyridine Nucleosides as Potential Antiviral Agents for the Treatment of Human Cytomegalovirus Infections," submitted as a Thesis to fulfill the requirements for a Ph.D. degree at the University of Michigan), a protected thiol derivative, a 2,5,6-trichloro-1-(5'-deoxy-5'-methylthio-β-D-ribofuranosyl)benzimidazole (17b) was selected as a synthetic target. 1,2,3-tri-O-acetyl-5'-deoxy-5'-methylthio-D-ribofuranose (15b) was synthesized as described by Montgomery et al. (See Montgomery, J. A. et al. (1974) *J. Med. Chem.* Vol. 17:1197–1209, incorporated herein by reference) and coupled to the 2,5,6-trichlorobenzimidazole under modified Vorbruggen conditions to give 2,5,6-trichloro-1-(2',3'-di-O-acetyl-5'-deoxy-5'-methylthio-β-D-ribofuranosyl)benzimidazole (16b) which was then deprotected to produce 17b.

Finally the azido compound 17a was synthesized by two different routes (see FIGS. 4 and 5). 1,2,3-tri-O-acetyl-5-deoxy-5-azido-β-D-ribofuranose (15a) was synthesized by methods well known to those of skill in the art and as described in Eur. Pat. Appl. EP 496,617, and incorporated herein by reference. The carbohydrate 15a was coupled with 2,5,6-trichlorobenzimidazole to give 2,5,6-trichloro- 1 -(2', 3'-di-O-acetyl-5'-deoxy-5'-azido-β-D-ribofuranosyl) benzimidazole (16a). Subsequent deprotection of 16a gave 17a. Compound 17a was also synthesized from 18 using Mitsunobo conditions. The reaction of 18 with triphenylphosphine, diethyl azidocarboxylate and diphenylphosphoryl azide gave 2,5,6-trichloro-1-(2',3'-O-isopropylidene-5'-deoxy-5'-azido-β-D-ribofuranosyl) benzimidazole (19a) which could then be deprotected to give 17a (see FIG. 5). When using the latter reaction sequence (FIG. 5) both 19a and 17a had to be purified by flash chromatography. Compound 15a could on the other hand be obtained in a pure form from 9 (shown in FIG. 4) without any chromatographic separations in the sequence.

Condensation of the 2',3'-acetylated carbohydrate derivatives with the 2,5,6-trichlorobenzimidazole under Vorbruggen conditions was employed to obtain all the benzimidazole nucleosides described herein. In accord with Baker's rule (See Baker, B. R., in The Ciba Foundation Symposium on the Chemistry and Biology of the Purines, Ed. G. E. W. Wolstenholme and C. M. O'Connors, Churchill, London, 1957, p.120) owing to 2'-O-acetyl participation during the condensation, the desired β-anomers (trans 1'-H and 2'-H) were obtained as the only isolated products.

For all the acetylated nucleosides 7a–d, 12a–d and 16a–b, the shift of the anomeric proton was between 6.19–6.28 ppm and the $J_{1',2'}$ coupling constants were 6.6–7.1 Hz. For all the deprotected nucleosides (8a–c, 13a–c, 17a–b) the signal for the anomeric proton appeared between 5.88–5.94 ppm and the $J_{1',2'}$ coupling constants were 7.2–7.9 Hz.

Previous reports of 2-substituted-1-(β-D-ribofuranosyl) benzimidazole nucleosides have indicated that the $J_{1',2'}$ couplings constant to be >5 Hz for such compounds (as reported in Vorbruggen, H. et al., (1981) Chem. Ber. Vol. 114:1234–1255; Kazimierczuk, Z. et al. (1982) Nucleosides and Nucleotides Vol. 1:275–287; and Kazimierczuk, Z. and Shugar, D. (1989) Nucleosides and Nucleotides Vol. 8:1379–1385). The observed anomeric coupling constants are thus consistent with the compounds having a β-conformation. The anomeric proton for 5'-deoxy-TCRB (2) appears at 5.86 ppm and has a J1',2' coupling constant of 6.4 Hz. The similarity of the shifts and coupling constants for compound 2 and the deprotected nucleosides 8a–d, 13a–d and 17a–b further suggests β-conformation. Finally compounds 13b and 17a were synthesized from pre-formed β-TCRB (through an isopropylidene derivative 18) as well as with Vorbruggen coupling reaction. The fact that both these routes gave the same final products as determined by 1H-NMR strongly suggests that compounds 13b and 17b both are β-anomers. Similarities in chemical shifts and coupling constants would then indicate that derivatives 8a–c, 13a, 13c and 17a are also β-anomers.

Melting points were taken on a Thomas-Hoover Unimelt apparatus and are uncorrected. Nuclear magnetic resonance (NMR) spectra were obtained at 360 or 300 MHz with Bruker WP 360 SY or Bruker 300 SY. The chemical shift values are reported in parts per million (ppm) relative to tetramethylsilane as an internal standard. UV spectra were obtained with a Kontron Uvikon 860 UV/VIS spectrophotometer. IR spectra were obtained on a Nicolet 5DXB FT-IR spectrophotometer. Elemental analysis were performed by the Analytical Laboratory of the Chemistry Department, University of Michigan. Flash column chromatography was performed using silica gel 60 230–400 mesh (ICN) and using a well known technique described by Still et al. (1978) J. Org. Chem. Vol. 43:2923–2925 and incorporated herein by reference. Thin layer chromatography (TLC) was performed on pre-scored Silica gel GHLF plates (Analtech, Newark, Del., USA). Compounds were visualized by illumination under UV light (254 nm) or by spraying with 20% methanolic sulfuric acid followed by charring on a hot plate. Evaporations were carried out under reduced pressure (water aspirator) with water bath temperatures below 40° C. unless otherwise specified. All solvents were dried prior to use as described by the handbook Purification of Laboratory Chemicals (Perrin, D. D.; Armarego, W. L. F., Purification of Laboratory Chemicals, 3rd Ed., Pergamon Press, N.Y. 1988, incorporated herein by reference) and stored over 4 Å sieves, under argon. Materials obtained from commercial suppliers were used without purification unless otherwise noted.

Specific Examples

General Procedure for the Synthesis of 5'-Substituted-Ribofuranoses: Compounds 6a–d, 11a–d, 15 a–b.

To the 1-O-methyl-2,3-O-isopropylidene ribose derivative (compound 4) was added 0.04N aq. HCl (50 mL) and the emulsion that formed upon stirring was heated at reflux for 2 h. This mixture was then cooled to room temperature. Amberlyst Ion Exchange Resin 47- OH— form was added to the mixture until a pH of 7 was reached. The resin was removed by filtration and washed with water (300 mL). The resulting aqueous solution was concentrated to a syrup under reduced pressure. This syrup was dissolved in dry pyridine (50 mL) and acetic anhydride (12.3 mL, 0.12 moles) was added. The reaction mixture was stirred for 24 hours at ambient temperature. Then the reaction mixture was poured into ice-cold saturated aqueous bicarbonate (200 mL) and the acetylated sugar extracted into $CHCl_3$ (3×100 mL). The organic phase was washed with water (2×100 mL), dried over magnesium sulfate, filtered and the solvent removed in vacuo to give compounds 6 a–d, 11 a–d, 15 a–b as syrups which were purified as described for each reaction below.

1,2,3-Tri-O-acetyl-5-O-methyl-D-ribofuranose (6a)

1-O-Methyl-2,3-O-isopropylidene-5-O-methyl-D-ribofuranose (5a, 2.15 g, 0.01 moles) gave after deprotection, acetylation and workup as described above, a brown oil which was chromatographed on a flash silica gel column (EtOAc/ hexane: 1/1 (v/v), 5 cm×20 cm). Elution yielded initially the pure β-anomer of 6a which was followed by a mixture of α- and β-anomers. Fractions containing the pure β-anomer were pooled and evaporated to dryness to give 1.4 g (48 %) of β-6a as a transparent syrup. Subsequent fractions were combined and concentrated to dryness to give 1.2 g (40 %) of a 1:3 mixture of α- and β-anomers as a white syrup. A small amount of β-anomer was crystallized out of MeOH for analytical purposes.

β-anomer: $R_f$ 0.71 (EtOAc/hexane ½ (v/v)), $^1$H-NMR (300 MHz, DMSO-$d_6$): δ 6.00 (s, 1H, 1-H), 5.21 (m, 2H, 2 and 3-H), 4.22 (m, 1H, 4-H), 3.50 (m, 2H, 5-H), 3.28 (s, 3H, $CH_3$), 2.00–2.11 (m, 9H, acetyls). Anal. Calcd. for $C_{12}H_{18}O_8$: C, 49.65; H, 6.25. Found: C, 49.70; H, 6.44.

1,2,3-Tri-O-acetyl-5-O-ethyl-D-ribofuranose (6b)

1-O-Methyl-2,3-O-isopropylidene-5-O-ethyl-D-ribofuranose (5b, 2.3 g, 0.01 moles) gave after deprotection, acetylation and workup as described in the general procedure a dark brown syrup. This syrup was chromatographed on a flash silica gel column (EtOAc/ hexane: ½ (v/v), 5 cm×20 cm). Elution yielded initially the pure β-anomer of 6b which was followed by a mixture of α- and β-anomers. Fractions containing the pure β-anomer were pooled and evaporated to dryness to give 1.3 g (44%) of β-6b as a transparent syrup. Subsequent fractions were combined and concentrated to dryness to give 1.4 g (43%) of a 1:3 mixture of α- and β-anomers as a syrup. A small amount of the β-anomer was crystallized out of MeOH for analytical purposes.

β-anomer: M.P. 58°–60° C. $R_f$ 0.50 (EtOAc/hexane 1/2 (v/v)), $^1$H-NMR (300 MHz, DMSO-$d_6$):δ 6.00 (s, 1H, 1-H), 5.23 (m, 2H, 2-H and 3-H), 4.20 (m, 1H, 4-H), 3.42–3.55 (m, 2H, 5-H, and $OCH_2$), 2.00–2.11 (m, 9H, acetyls), 1.09 (t, 3H, $OCH_2CH_3$). Anal. Calcd. for $C_{13}H_{20}O_8$: C, 51.31; H, 6.63. Found: C, 51.52; H, 6.81.

1,2,3-Tri-O-acetyl-5-O-butyl-D-ribofuranose (6c)

1-O-Methyl-2,3-O-isopropylidene-5-O-butyl-D-ribofuranose (5c, 5.4 g, 0.02 moles) gave after deprotection, acetylation and workup as described in the general procedure a yellow syrup. This syrup was chromatographed on a flash silica gel column (EtOAc/ hexane: ½ (v/v), 5 cm×20 cm). Elution yielded initially the pure β-anomer of 6c, which was followed by a mixture of α- and β-anomers. Fractions containing the pure β-anomer were pooled and evaporated to dryness to give 1.0 g (14 %) of β-6a as a transparent syrup. Subsequent fractions were combined and concentrated to dryness to give 4.2 g (64 %) of a 1:9 mixture of α- and β-anomers as a white syrup.

β-anomer: $R_f$ 0.31 (EtOAc/hexane ½ (v/v)), $^1$H-NMR (300 MHz, DMSO-$d_6$):δ 6.00 (s, 1H, 1-H), 5.26–5.18 (m, 2H, 2-H and 3-H), 4.21 (m, 1H, 4-H), 3.52–3.39 (m, 2H, 5-H and OCH$_2$), 1.98–2.11 (m, 9H, acetyls), 1.45 (m, 2H, CH$_2$), 1.31 (m, 2H, CH$_2$), 0.87 (t, 3H, CH$_3$). Anal. Calcd. for C$_{15}$H$_{24}$O$_8$: C, 54.21; H, 7.28. Found: C, 54.27; H, 7.60.

1,2,3-Tri-O-acetyl-5-O-hexyl-D-ribofuranose (6d)

1-O-Methyl-2,3-O-isopropylidene-5-O-hexyl-D-ribofuranose (5d, 5.0 g, 0.017 moles) gave after deprotection, acetylation and workup as described in the general procedure a brown syrup. The syrup was chromatographed on a flash silica gel column (EtOAc/hexane: ½ (v/v), 5 cm×20 cm). Elution gave a mixture of α- and β-anomers. These fractions were pooled and evaporated to dryness to give 3.75 g (59 %) of 6d as a 1:5 mixture of α- and β-anomers, which were not separated.

$^1$H-NMR (300 MHz, DMSO-d$_6$):δ 6.27 (t, 1H,$_{J1',2'}$=2.3 Hz, 1-H-a), 6.00 (s, 1H, 1-H-b), 5.19–5.26 (m, 2H, 2-H and 3-H a and b), 4.30 (m, 1H, 4-H-a), 4.22 (q, 1H, 4-H-b), 3.38–3.56 (m, 4H, 5-H, a and b and OCH$_2$), 1.94–2.18 (m, 9H, acetyls), 1.47 (m, 2H, OCH$_2$CH$_2$(CH$_2$)CH$_3$), 1.29 (m, 6H, CH$_2$s), 0.86 (t, 3H, CH$_3$) Anal. Calcd. for C$_{17}$H$_{28}$O$_8$: C, 56.65; H, 7.83. Found: C, 56.78; H, 7.93.

1,2,3-Tri-O-acetyl-5-deoxy-5-fluoro-β-D-ribofuranose (11a)

1-O-Methyl-2,3-O-isopropylidene-5-deoxy-5-fluoro-β-D-ribofuranose (10a, 2.5 g, 0.012 moles) gave after deprotection, acetylation, workup as described in the general procedure above and crystallization of the crude reaction mixture from MeOH, 2.0 g (60%) yield of 11a as white crystals of the pure β-anomer.

Mp: 95°–6° C. R$_f$ 0.57 (EtOAc/hexane ½ (v/v)), $^1$H-NMR (300 MHz, DMSO-d$_6$):δ 6.04 (s, 1H, 1-H), 5.21–5.30 (m, 2H, 2-H), 4.29–4.71 (m, 3H, 4-H and 5-H), 2.01–2.10 (s, 9H, acetyls).

1,2,3-Tri-O-acetyl-5-deoxy-5-chloro-β-D-ribofuranose (11b)

1-O-Methyl-2,3-O-isopropylidene-5-deoxy-5-chloro-D-ribofuranose 10b (3.0 g, 0.018 moles) gave after deprotection, acetylation, workup as described above and crystallization of the reaction mixture from MeOH 2.7 g (50 %) yield of the pure β-anomer of 11b as white crystalline solid.

Mp: 81°–82° C. R$_f$0.65 (EtOAc/hexane ½ (v/v)). $^1$H-NMR (300 MHz, DMSO-d$_6$):δ 6.02 (s, 1H, 1-H), 5.24–5.31 (m, 2H, 2-H and 3-H) ,4.38 (m, 1H, 4-H), 3.89 (dd, Hz, 1H, 5-H, J$_{4',5'}$=4.4 Hz, J$_{5'a,5'b}$=12), 3.78 (dd, 1H, 5-H, J$_{4',5'}$=4.9 Hz, J$_{5'a,5'b}$=12), 2.10 (s, 3 H, acetyl), 2.07 (s, 3H, acetyl), 2.04 (s, 3 H, acetyl) Anal. Calcd. for C$_{11}$H$_{15}$ClO$_7$: C, 44.83; H, 5.13. Found: C, 44.79; H, 5.24.

1,2,3-Tri-O-acetyl-5-deoxy-5-bromo-β-D-ribofuranose (11c)

1-O-Methyl-2,3-O-isopropylidene-5-deoxy-5-bromo-D-ribofuranose (10c, 4 g, 0.01 moles) gave after deprotection, acetylation, workup as described above and crystallization of the reaction mixture from MeOH 1.5 g (44%) of a pure β-anomer of 11c as white crystalline solid.

Mp.: 96°–97° C. R$_f$0.70 (EtOAc/hexane ½). $^1$H-NMR (360 MHz, DMSO-d$_6$):δ 6.03 (s, 1H, 1-H), 5.26 (m, 2H, 2-H and 3-H), 4.37 (m, 1H, 4-H), 3.75 (dd, 1H, 5-H, J$_{4',5'}$=5.0 Hz, J$_{5'a,5'b}$=11.2 Hz), 3.66 (dd, 1H, 5-H, J$_{4',5'}$=5.0 Hz, J$_{5'a,5}$b= 11.2 Hz), 2.04–2.10 (m, 9 H, acetyls). Anal. Calcd. for C$_{11}$H$_{15}$BrO$_7$: C, 38.96; H, 4.46. Found: C, 39.15; H, 4.44.

1,2,3-Tri-O-acetyl-5-deoxy-5-iodo-3-D-ribofuranose (11d)

1-O-Methyl-2,3-O-isopropylidene-5-deoxy-5-iodo-D-ribofuranose (10d ,6.3 g, 0.02 moles) gave after deprotection, acetylation, workup as described above and recrystallization of the crude reaction mixture from MeOH 5.2 g (67 %) yield of 11d as white crystals of the pure β-anomer.

Mp: 86°–88° C. R$_f$ 0.49 (EtOAc/hexane ½ (v/v)), $^1$H-NMR (360 MHz, DMSO-d$_6$):δ 6.03 (s, 1H, 1-H), 5.26 and 5.16 (d and q respectively, 2H, 2-H and 3-H), 4.15 (q, 1H, 4-H), 3.49 and 3.40 (2q, 2H, 5-H), 2.09 (s, 3H, acetyl), 2.04 (s, 3H, acetyl).

1,2,3-Tri-O-acetyl-5-deoxy-5-azido-β-D ribofuranose (15a)

1-O-Methyl-2,3-O-isopropylidene-5-deoxy-5-azido-D-ribofuranose (14a, 4g, 0.017 moles) gave after deprotection, acetylation, workup as described above and crystallization of the crude reaction mixture from MeOH gave 3.0 g (60%) of the pure β anomer of 15a as white crystalline solid.

R$_f$ 0.4 (EtOAc/hexane ½ (v/v)), $^1$H-NMR (300 MHz, DMSO-d$_6$):δ 6.06 (s, 1H, 1-H), 5.27 (m, 2H, 2-H and 3-H), 4.31 (m, 1H,4-H), 3.72 (dd, 1H, 5-H, J$_{4',5'}$=3.4 Hz, J$_{5'a,5'b}$=13.7 Hz), 3.34 (dd, 1H, 5-H, J$_{4',5'}$=3.4 Hz, J$_{5'a,5'b}$=13,7 Hz), 2.04–2.10 (m, 9H, acetyls).

1,2,3-Tri-O-acetyl-5-deoxy-5-methylthio-β-D-ribofuranose (15b)

1-O-Methyl-2,3-O-isopropylidene-5-deoxy-5-methylthio-D-ribofuranose (14b, 2.0 g, 8 mmoles) gave after deprotection, acetylation, workup as described above and crystallization of the reaction mixture from MeOH 1.8 g (74%) of the β-anomer of 15b as a white crystalline solid.

Mp: 66° C. R$_f$ 0.47 (EtOAc/hexane ½ (v/v)), $^1$H-NMR (300 MHz, DMSO-d$_6$): 6.00 (s, 1H, 1-H), 5.1–5.3 (m, 2H, 2-H and 3-H) ,4.29–4.40 (m, 1H, 4-H), 2.73–2.79 (m, 2H, 5-H), 2.01–2.10 (m, 12 H, acetyls and SCH$_3$).

General Procedure for the Vorbruggen Condensation to Synthesize 5'-Substituted-Ribofuranosyl Benzimidazoles: Compounds 7a-d. 12a–d and 16 a–b 2,5,6-Trichlorobenzimidazole (0.6 g, 2 mmol) were placed in a flame dried flask under an argon atmosphere. Dry CH$_3$CN (10 mL) and BSA (0.5 mL, 2 mmol) was added and the reaction mixture stirred at room temperature for 30 min. The appropriate acetylated carbohydrate (2 mmol) dissolved in dry CH$_3$CN (10 mL) was added to the reaction mixture via a canula. Finally TMSOTf (0.47 mL, 2.4 mmol) was added and the reaction mixture was stirred at room temperature for 15 min. Saturated NaHCO$_3$ (20 mL) was added to quench the reaction. The reaction mixture was extracted with EtOAc (3×80 mL). The combined organic phase was washed with saturated NaCl solution, decolorized with charcoal, dried over magnesium sulfate, filtered and evaporated to dryness. The syrup or solid obtained was purified as described for each individual reaction below. Analogous methods may be used for the preparation of other 5'-substituted-benzimidazoles by employing other benzimidazoles, such as those described in detail above.

2,5,6-Trichloro-1-(2',3'-di-O-acetyl-5'-O-methyl-β-D-ribofuranosyl)benzimidazole (7a)

Compound 6a (0.75 g, 3.4 mmol) was coupled to 2,5,6-trichlorobenzimidazole (0.8 g, 3.6 mmol) under Vorbruggen conditions, to give after workup as described above a solid. This solid was purified by chromatography (EtOAc/hexane 1/1(v/v), 2 cm×15 cm), the fractions that contained the nucleoside were pooled and evaporated to dryness to afford after recrystallization from MeOH 0.92 g (60%) of 7a as a white crystalline solid.

Mp: 150°–151° C. R$_f$ 0.51 (EtOAc/hexane 1/1 (v/v)), R$_f$ 0.67 (EtOAc/hexane 5/1 (v/v)). $^1$H-NMR (300 MHz, DMSO-$d_6$):δ 8.34 (s, 1H, $C_7$-H), 8.00 (s, 1H, $C_4$-H), 6.19 (d, 1H,1'-H, $J_{1',2'}$=7.0 Hz), 5.45 (m, 2H,2'-H and 3'-H), 4.44 (m, 1H, 4'-H), 3.75 (m, 2H, 5'-H), 3.52 (s, 3H, $OCH_3$), 2.16 (s, 3H, acetyl), 1.98 (s, 3H, acetyl). Anal. Calcd. for $C_{17}H_{17}Cl_3N_2O_6$: C, 45.205; H, 3.794; N, 6.202. Found: C, 45.59; H, 3.76; N, 5.87.

2,5,6-Trichloro-1-(2',3'-di-O-acetyl-5'-O-ethyl-β-D-ribofuranosyl)benzimidazole (7b)

Compound 6b (1.2 g, 3.9 mmol) was coupled to 2,5,6-trichlorobenzimidazole (0.87 g, 3.9 mmol) under Vorbruggen conditions, to give after workup as described above a solid. This solid was purified by chromatography (EtOAc/hexane 1/1(v/v), 4 cm×15 cm), the fractions that contained the nucleoside were pooled and evaporated to dryness to afford after recrystallization from MeOH 2 g (78 %) of 7b as a white crystalline solid.

Mp: 125°–126° C. $R_f$ 0.42 (EtOAc/hexane 1/1 (v/v)), $R_f$ (EtOAc/hexane 5/1 (v/v)). $^1$H-NMR (300 MHz, DMSO-$d_6$): δ 8.27 (s, 1H, $C_7$-H), 7.99 (s, 1H, $C_4$-H), 6.19 (d, 1H,1'-H, $J_{1',2'}$=6.7 Hz), 5.45 (m, 2H,2'-H and 3'-H), 4.44 (m, 1H, 4'-H), 3.55–3.84 (m, 4H, 5'-H and $OCH_2CH_3$), 2.16 (s, 3H, acetyl), 1.99 (s, 3H, acetyl), 1.28 (t, 1H, $OCH_2CH_3$). Anal. Calcd. for $C_{18}H_{19}Cl_3N_2O_6$: C,46.423; H, 4.112; N, 6.015. Found: C, 46.34; H, 4.16; N, 5.85.

2,5,6-Trichloro-1-(2',3'-di-O-acetyl-5'-O-butyl-β-D-ribofuranosyl)benzimidazole (7c).

Compound 6c (2 g, 6.0 mmol) was coupled to 2,5,6-trichlorobenzimidazole (1.2 g, 5.4 mmol) under Vorbruggen conditions, to give after workup as described above a viscous syrup. This syrup was purified by chromatography (EtOAc/hexane 1/1 (v/v), 4 cm×15 cm), the fractions that contained the nucleoside were pooled and evaporated to dryness to afford after recrystallization from MeOH 1.5 g (55%) of 7c as a white crystalline solid.

Mp: 143°–144° C. $R_f$ 0.47 (EtOAc/hexane 1/1 (v/v)), $R_f$ 0.69 (EtOAc/hexane 5/1 (v/v)). $^1$H-NMR (300 MHz, DMSO-$d_6$):δ 8.24 (s, 1H, $C_7$-H), 7.97 (s, 1H, $C_4$-H), 6.19 (d, 1H, 1'-H, $J_{1',2'}$=7.0 Hz), 5.44 (m, 2H, 2'-H and 3'-H), 4.43 (m, 1H, 4'-H), 3.49–3.83 (m, 4H, 5'-H and $OCH_2R$) 2.15 (s, 3H, acetyl), 1.98 (s, 3H, acetyl), 1.65 (m, 2H, $OCH_2CH_2CH_2R$), 1.40 (m, 2H, $OCH_2CH_2CH_2R$), 0.89 (t, 3H, -$CH_3$). Anal. Calcd. for $C_{20}H_{23}Cl_3N_2O_6$: C, 48.65; H, 4.695; N, 5.673. Found: C, 48.41; H, 4.67; N, 5.49.

2,5,6-Trichloro-1-(2',3'-di-O-acetyl-5'-O-hexyl-β-D-ribofuranosyl)benzimidazole (7d)

Compound 6d (1.6 g, 4.4 mmol) was coupled to 2,5,6-trichlorobenzimidazole (0.89 g, 4.0 mmol) under Vorbruggen conditions, to give after workup as described above a syrup. This syrup was purified by chromatography (EtOAc/hexane 1/1(v/v), 4 cm×15 cm), the fractions that contained the nucleoside were pooled and evaporated to dryness to afford after recrystallization from MeOH 1.3 g (60%) of 7d as a white crystalline solid.

Mp: 98°–100° C. $R_f$ 0.47 (EtOAc/hexane 1/2 (v/v)), Rf (EtOAc/hexane 5/1 (v/v)). $^1$H-NMR (300 MHz, DMSO-$d_6$): δ 8.25 (s, 1H, $C_7$-H), 8.00 (s, 1H, $C_4$-H), 6.19 (d, 1H,1'-H, $J_{1',2'}$=6.9 Hz), 5.44 (m, 2H,2'-H and 3'-H), 4.43 (m, 1H, 4'-H), 3.49–3.83 (m, 4H, 5'-H and $OCH_2R$) 2.15 (s, 3H, acetyl), 1.98 (s, 3H, acetyl), 1.67 (m, 2H, $OCH_2CH_2CH_2R$), 1.25–1.37(m, 6H, $OCH_2CH_2(CH_2)_3CH_3$), 0.82(t, 3H, $OCH_2CH_2(CH_2)_3CH_3$). Anal. Calcd. for $C_{22}H_{27}Cl_3N_2O_6$: C, 50.64; H, 5.22; N, 5.37. Found: C, 50.64; H, 5.16; N, 5.29.

2,5,6-Trichloro-1-(2',3'-di-O-acetyl-5'-deoxy-5'-fluoro-β-D-ribofuranosyl) benzimidazole (12a)

Compound 11a (0.9 g, 3.2 mmol) was coupled to 2,5,6-trichlorobenzimidazole (0.8 g, 3.6 mmol) under Vorbruggen conditions. The reaction mixture was worked up as described in the general procedure and gave after crystallization from MeOH 1.2 g (87%) of 12a as a white crystalline solid.

Mp: 128°–129° C. $R_f$ 0.70 (EtOAc/hexane 5/1 (v/v)). $^1$H-NMR (360 MHz, DMSO-$d_6$):δ 8.04 (d, 1H, $C_4$-H, $J_{C4,F}$=1.9 Hz), 8.02 (s, 1H, $C_7$-H), 6.28 (d, 1H, 1'-H, $J_{1',2'}$=6.6 Hz), 5.46–5.55 (m, 2H, 2'-H and 3'-H), 4.87 (dm, 2H, 5'-H, $J_{5',F}$=47 Hz, $J_{4',5'}$=3.6 Hz), 4.53 (m, 1H, 4'-H, $J_{4',F}$=29 Hz, $J_{4',5'}$=3.6 Hz), 2.15 (s, 3H, acetyl), 2.01 (s, 3H, acetyl). Anal. Calcd. for $C_{16}H_{14}Cl_3FN_2O_5$: C, 43.71; H, 3.21; N, 6.37. Found: C, 43.41; H, 3.53; N, 6.05.

2,5,6-Trichloro-1-(2',3'-di-O-acetyl-5'-deoxy-5'-chloro-β-D-ribofuranosyl) benzimidazole (12b)

Compound 11b (1.0 g, 3.4 mmol) was coupled to 2,5,6-trichlorobenzimidazole (0.7 g, 3.1 mmol) under Vorbruggen conditions, to give after workup as described above a solid. This solid was purified by chromatography (EtOAc/hexane 1/2 (v/v), 4 cm×15 cm), the fractions that contained the nucleoside were pooled and evaporated to dryness to afford after recrystallization from EtOAc/hexane 1.5 g (55 %) of 12b as a white crystalline solid.

Mp: 160°–161° C. $R_f$ 0.26 (EtOAc/hexane 1/2 (v/v)), $R_f$ 0.67 (EtOAc/hexane 5/1(v/v)). $^1$H-NMR (300 MHz, DMSO-$d_6$):δ 8.21 (s, 1H, $C_7$-H), 8.01 (s, 1H, $C_4$-H), 6.28 (d, 1H, 1'-H, $J_{1',2'}$=7.1 Hz), 5.59 (t, 1H, 2'-H, $J_{1',2'}$=7.3 Hz), 5.46 (q, 1H, 3'-H, $J_{2',3'}$=7.3 Hz, $J_{3',4'}$=4.7 Hz), 4.50 (q, 1H, 4'-H, $J_{3',4'}$=4.7 Hz), 4.15 (m, 2H, 5'-H), 2.14 (s, 3H, acetyl), 2.02 (s, 3H, acetyl). Anal. Calcd. for $C_{16}H_{14}Cl_4N_2O_5$: C, 42.13; H, 3.09; N, 6.14. Found: C, 42.33; H, 3.15; N, 6.02.

2,5,6-Trichloro-1-(2',3'-di-O-acetyl-5'-deoxy-5'-bromo-β-D-ribofuranosyl) benzimidazole (12c)

Compound 11c (0.5 g, 1.5 mmol) was coupled to 2,5,6-trichlorobenzimidazole (0.33 g, 1.5 mmol) under Vorbruggen conditions to give after the workup described in the general procedure a solid. This solid gave after recrystallization from MeOH, 0.7 g (95%) of 12c as a white crystalline solid.

Mp: 150°–152° C. $R_f$ 0.51 (EtOAc/hexane 1/2 (v/v)), $R_f$ 0.67 (EtOAc/hexane 5/1 (v/v)). $^1$H-NMR (300 MHz, DMSO-$d_6$):δ 8.25 (s, 1H, $C_7$-H), 8.02 (s, 1H, $C_4$-H), 6.28 (d, 1H, 1'-H, $J_{1',2'}$=7.1 Hz), 5.63 (t, 1H, 2'-H, $J_{1',2'}$=7.2 Hz), 5.43 (q, 1H, 3'-H, $J_{2',3'}$=7.3 Hz, $J_{3',4'}$=4.7 Hz), 4.48 (q, 1H, 4'-H, $J_{3',4'}$=4.7 Hz, $J_{4',5'}$=9.9 Hz), 3.94–4.08 (m, 2H, 5'-H), 2.14 (s, 3H, acetyl), 2.01 (s, 3H, acetyl). Anal. Calcd. for $C_{16}H_{14}BrCl_3N_2O_5$ :C, 38.39; H, 2.82; N, 5.59. Found: C, 38.33; H, 2.77; N, 5.36.

2,5,6-Trichloro-1-(2',3'-di-O-acetyl-5'-deoxy-5'-iodo-β-D-ribofuranosyl) benzimidazole (12d)

Compound 11d (1.5 g, 5.2 mmol) was coupled to 2,5,6-trichlorobenzimidazole (1.0 g, 4.7 mmol) under Vorbruggen conditions, to give after workup as described above a solid. This solid was purified by chromatography (EtOAc/hexane 1/1 (v/v), 4 cm×15 cm), the fractions that contained the nucleoside were pooled and evaporated to dryness to afford after recrystallization from MeOH, 1.8 g (70%) of 12d as a white crystalline solid.

Mp: 170°–171° C. $R_f$ 0.31 (EtOAc/hexane 1/2 (v/v)), Rf (EtOAc/hexane 5/1 (v/v)). $^1$H-NMR (300 MHz, DMSO-$d_6$): δ 8.26 (s, 1H, $C_7$-H), 8.01 (s, 1H, $C_4$-H), 6.26 (d, 1H, 1'-H, $J_{1',2'}$=7.1 Hz), 5.69 (t, 1H, 2'-H, $J_{1',2'}$=7.2 Hz), 5.38 (q, 1H, 3'-H, $J_{2',3'}$=7.2 Hz, $J_{3',4'}$=4.8 Hz), 4.31 (m, 1H, 4'-H), 4.31 (dd, 1H, 5'-H, $J_{4',5'}$=5.3 Hz, $J_{5'a,5'b}$=10.7 Hz), 3.80 (dd, 1H, 5'-H, $J_{4',5'}$=6.5 Hz, $J_{5'a,5'b}$=10.7 Hz), 2.15 (s, 3H, acetyl), 2.01 (s, 3H, acetyl). Anal. Calcd. for $C_{16}H_{14}Cl_3IN_2O_5$: C, 35.10; H, 2.58; N, 5.12. Found: C, 35.13; H, 2.57; N, 5.06.

2,5,6-Trichloro-1-(2',3'-di-O-acetyl-5'-deoxy-5'-azido-β-D-ribofuranosyl) benzimidazole (16a)

Compound 15a (1.3 g, 4.3 mmol) was coupled to 2,5,6-trichlorobenzimidazole (0.9 g, 3.9 mmol) under Vorbruggen conditions, to give after workup as described above a solid. This solid was purified by chromatography (EtOAc/hexane 1/1 (v/v), 4 cm×15 cm), the fractions that contained the nucleoside were pooled and evaporated to dryness to afford after recrystallization from MeOH, 1.4 g (75%) of 16a as a white crystalline solid.

Mp: 149°–150° C. $R_f$ 0.35 (EtOAc/hexane 1/1 (v/v)), $R_f$ 0.62 (EtOAc/hexane 5/1(v/v)). $^1$H-NMR (360 MHz, DMSO-$d_6$):δ 8.23 (s, 1H, $C_7$-H), 8.02 (s, 1H, $C_4$-H), 6.26 (d, 1H, 1'-H, $J_{1',2'}$=7.0 Hz), 5.61 (t, 1H, 2'-H, $J_{1',2'}$=7.0 Hz), 5.41 (q, 1H, 3'-H, $J_{2',3'}$=7.1 Hz, $J_{3',4'}$=4.8 Hz), 4.38 (m, 1H, 4'-H), 3.91 (m, 2H, 5'-H), 2.13 (s, 3H, acetyl), 2.02 (s, 3H, acetyl). Anal. Calcd. for $C_{16}H_{14}Cl_3N_5O_5$: C, 41.54; H, 3.05; N, 15.14. Found: C, 41.53; H, 2.85; N, 14.92.

2,5,6-Trichloro-1-(2',3'-di-O-acetyl-5'-deoxy-5'-methylthio-β-D-ribofuranosyl) benzimidazole (16b)

Compound 15b (2.3 g, 7.4 mmol) was coupled with 2,5,6-trichlorobenzimidazole (1.5 g, 7.4 mmol) under Vorbruggen conditions, to give after workup as described above a solid. This solid was purified by chromatography (EtOAc/hexane 1/1(v/v), 4 cm'15 cm), the fractions that contained the nucleoside were pooled and evaporated to dryness to afford after recrystallization from MeOH, 2.1 g (65%) of 16b as a white crystalline solid.

$R_f$ 0.40 (EtOAc/hexane 1/1 (v/v)), $R_f$ 0.83 (EtOAc/hexane 5/1 (v/v)). $^1$H-NMR (360 MHz, DMSO-$d_6$):δ 8.21 (s, 1H, $C_7$-H), 8.00 (s, 1H, $C_4$-H), 6.21 (d, 1H, 1'-H, $J_{1',2'}$=6.8 Hz), 5.64 (t, 1H, 2'-H, $J_{1',2'}$=7.1 Hz), 5.43 (q, 1H, 3'-H, $J_{2',3'}$=7.3 Hz, $J_{3',4'}$=5.3 Hz), 4.37 (m, 1H, 4'-H), 3.01–3.10 (m, 2H, 5'-H), 2.13 (s, 3H, $SCH_3$), 2.11 (s, 3H, acetyl), 2.01 (s, 3H, acetyl). Anal. Calcd. for $C_{17}H_{17}Cl_3N_2O_5S$: C, 43.65; H, 3.66; N, 5.99. Found: C, 43.65; H, 3.90; N, 6.01.

General Procedure for Deprotection to Synthesize 5'-Substituted-Ribofuranosyl Benzimidazoles: Compounds 8a–d 13a–d and 17a–b The appropriate acetylated nucleoside (1 mmol) was dissolved in EtOH/$H_2O$ 2/1 (v/v) and $Na_2CO_3$ (2 mmol) was added to the solution. The reaction mixture was stirred for 4 hours, and then neutralized to pH 7 with glacial acetic acid. The EtOH was removed under reduced pressure and the solid that formed was collected by filtration. This solid was finally recrystallized to give pure deprotected nucleosides.

2,5,6-Trichloro-1-(5'-O-methyl-β-D-ribofuranosyl) benzimidazole (8a)

Compound 7a (0.3 g, 6.6 mmol) was deprotected as described above and recrystallized twice from MeOH to give 0.2 g (80%) of 8a as white crystals.

Mp: 104°–105° C. $R_f$ 0.43 (EtOAc/hexane 5/1 (v/v)). $^1$H-NMR (360 MHz, DMSO-$d_6$):δ 8.33 (s, 1H, $C_7$-H), 7.97 (s, 1H, $C_4$-H), 5.89 (d, 1H,1'-H, $J_{1',2'}$=7.8 Hz), 5.54 (d, 1H, 2'-OH, $J_{2',2'-OH}$=6.3 Hz, $D_2O$ exchangeable), 5.38 (d, 1H, 3'-OH, $J_{3',3'-OH}$=3.6 Hz), 4.37 (m, 1H, 2'-H, collapses to a triplet on $D_2O$ wash, $J_{1',2'}$=7.8 Hz), 4.11 (m, 2H, 3'-H and 4'-H), 3.65 (m, 2H, 5'-H), 3.47 (s, 3H, $OCH_3$). $^{13}$C-NMR (90.556 MHz, $d_6$-DMSO):δ 142.243, 141.036, 132.255, 125.866, 125.798,120.226, 114.713, 89.219, 84.710, 72.040, 71.677, 70.045, 58,613. Anal. Calcd. for $C_{13}H_{13}Cl_3N_2O_4$: C, 42.47; H, 3.56; N, 7.62. Found: C, 42.32; H, 3.72; N, 7.52.

2,5,6-Trichloro-1-(5'-O-ethyl-β-D-ribofuranosyl) benzimidazole (8b)

Compound 7b (0.3 g, 6.4 mmol) was deprotected as described above and recrystallized twice from MeOH to give 0.19 g (78%) of 8b as white crystals.

Mp: 88°–90° C. $R_f$ 0.47 (EtOAc/hexane 5/1 (v/v)). $^1$H-NMR (360 MHz, DMSO-$d_6$):δ 8.25 (s, 1H, $C_7$-H), 7.98 (s, 1H, $C_4$-H), 5.89 (d, 1H, 1'-H, $J_{1',2'}$=7.8 Hz), 5.54 (d, 1H, 2'-OH, $J_{2',2'-OH}$=6.4 Hz, $D_2O$ exchangeable), 5.38 (d, 1H, 3'-OH, $J_{3',3'-OH}$=4.4 Hz), 4.36 (m, 1H, 2'-H, collapses to a triplet on $D_2O$ wash, $J_{1',2'}$=7.8 Hz), 4.12 (m, 2H, 3'-H and 4'-H), 3.56–3.73 (m, 4H, 5'-H and $OCH_2CH_3$), 1.26 (s, 3H, $OCH_2CH_3$). $^{13}$C-NMR (90.556 MHz, $d_6$-DMSO):δ 142.285, 141.085, 132.270, 125.882 (2C),120.309, 114.436, 89.121, 84.754, 71.791, 69.994, 69.660, 66.202, 14.990. Anal. Calcd. for $C_{14}H_{15}Cl_3N_2O_4$: C, 44.06; H, 3.96; N, 7.34. Found: C, 43.74; H, 4.19; N, 7.21.

2,5,6-Trichloro-1-(5'-O-butyl-β-D-ribofuranosyl) benzimidazole (8c)

Compound 7c (0.4 g, 8.1 mmol) was deprotected as described above and recrystallized twice from MeOH to give 0.23 g (80%) of 8c as white crystals.

Mp: 70°–72° C. $R_f$ 0.51 (EtOAc/hexane 5/1 (v/v)). $^1$H-NMR (360 MHz, DMSO-$d_6$):δ 8.23 (s, 1H, $C_7$-H), 7.98 (s, 1H, $C_4$-H), 5.89 (d, 1H, 1'-H, $J_{1',2'}$=7.9 Hz), 5.54 (d, 1H, 2'-OH, $J_{2',2'-OH}$=6.4 Hz, $D_2O$ exchangeable), 5.38 (d, 1H, 3'-OH, $J_{3',3'-OH}$=4.3 Hz), 4.36 (q, 1H, 2'-H, $J_{1',2'}$=7.9 Hz, $J_{2',3'}$=6.4, collapses to a triplet on $D_2O$ wash, $J_{1',2'}$=7.5 Hz), 4.11 (m, 2H, 3'-H and 4'-H), 3.62–3.74 (m, 4H, 5'-H and $OCH_2CH_2$—), 1.64 (m, 2H, $OCH_2CH_2$—), 1.36 (m, 2H, $OCH_2CH_2CH_2CH_3$), 0.90 (t, 3H, $OCH_2CH_2CH_2CH_3$), $^{31}$C-NMR (90.556 MHz, $d_6$-DMSO):δ 142.294, 141.085, 132.256, 125.875 (2C),120.307, 114.387, 89.096, 84.806, 71.797, 70.585, 70.008, 69.951, 31.102, 18.835, 13.780. Anal.Calcd. for $C_{16}H_{19}Cl_3N_2O_4$: C, 46.91; H, 4.67; N, 6.84. Found: C, 47.27; H, 4.86; N, 6.71.

2,5,6-Trichloro-1-(5'-deoxy-5'-fluoro-β-D-ribofuranosyl) benzimidazole (13a)

Compound 12a (0.3 g, 7.1 mmol) was deprotected as described above and recrystallized twice from MeOH to give 0.21 g (81%) of 13a as white crystals.

Mp: 132°–133° C. $R_f$ 0.46 (EtOAc/hexane 5/1 (v/v)). $^1$H-NMR (360 MHz, DMSO-$d_6$):δ 8.01 (s, 1H, $C_4$-H), 7.92 (d, 1H, $C_7$-H, J=3.1 Hz), 5.94 (d, 1H, 1'-H, $J_{1',2'}$=7.5 Hz), 5.67 (d, 1H, 2'-OH, $J_{2',2'-OH}$=6.3 Hz, $D_2O$ exchangeable), 5.53 (d, 1H, 3'-OH, $J_{3',3'-OH}$=4.7 Hz), 4.67–4.89 (two octuplets, 2H, 5'-H, $J_{2',F}$=47.1 Hz) 4.38 (m, 1H, 2'-H, collapses to a triplet on $D_2O$ wash, $J_{1',2'}$=7.5 Hz), 4.13–4.23 (m, 2H, 3'-H and 4'-H, $J_{3',F}$=33 Hz). $^{13}$C-NMR (90.556 MHz, $d_6$-DMSO):δ 142.269, 141.056, 132.321, 126.119, 125.119, 120.445, 113.652 (J=7.3 Hz, long range coupling with F), 89.334 (1'-C), 83,746 (4'-C, J=18.0 Hz), 83.180 (5'-C, J=167.5 Hz), 71.546 (2'-C), 68.897 (3'-C, J=4.9 Hz). MS (EI 70 eV with DCI probe) Calcd. 353.9741, Found 353.9746. Anal.Calcd. for $C_{12}H_{10}Cl_3FN_2O_3$: C, 40.53; H, 2.83; N, 7.88. Found: C, 40.24; H, 2.66; N, 7.67.

2,5,6-Trichloro-1-(5'-deoxy-5'-chloro-β-D-ribofuranosyl) benzimidazole (13b)

Compound 12b (0.2 g, 4.4 mmol) was deprotected as described above and recrystallized twice from MeOH to give 0.12 g (75%) of 13b as white crystals.

Mp: 160°–161° C. $R_f$ 0.53 (EtOAc/hexane 5/1 (v/v)). $^1$H-NMR (360 MHz, DMSO-$d_6$):δ 8.06 (s, 1H, $C_7$-H), 8.00 (s, 1H, $C_4$-H), 5.91 (d, 1H, 1'-H, $J_{1',2'}$=7.5 Hz), 5.66 (d, 1H, 2'-OH, $J_{2',2'-OH}$=5.4 Hz, $D_2O$ exchangeable), 5.52 (d, 1H, 3'-OH, $J_{3',3'}$-OH=3.9 Hz), 4.49 (q, 1H, 2'-H,$J_{2',2'-OH}$=5.3 Hz, collapses to a triplet on $D_2O$ wash, $J_{1',2'}$=7.4 Hz), 4.18–3.98 (m, 4H, 3'-H, 4'-H and 5'-H). $^{13}$C-NMR (90.556 MHz, $d_6$-DMSO):δ 142.244, 140.967, 132.313, 126.178, 125.989, 120.373, 113.854, 89.146, 83.987, 71.092, 69.947, 44.769. Anal.Calcd. for $C_{12}H_{10}Cl_4N_2O_3$: C, 38.74; H, 2.71; N, 7.53. Found: C, 38.57; H, 2.58; N, 7.54.

2,5,6-Trichloro-1-(5'-deoxy-5'-bromo-β-D-ribofuranosyl) benzimidazole (13c)

Compound 12c (0.2 g, 4.0 mmol) was deprotected as described above and recrystallized twice from MeOH to give 0.14 g (82%) of 13c as white crystals.

Mp: 159°–160° C. $R_f$ 0.50 (EtOAc/hexane 5/1 (v/v)). $^1$H-NMR (360 MHz, DMSO-$d_6$):δ 8.09 (s, 1H, $C_7$-H), 8.01 (s, 1H, $C_4$-H), 5.91 (d, 1H, 1'-H, $J_{1',2'}$=7.2 Hz), 5.66 (m, 1H, 2'-OH, $D_2O$ exchangeable), 5.54 (m, 1H, 3'-OH, $D_2O$ exchangeable), 4.53 (m, 1H, 2'-H, collapses to a triplet on $D_2O$ wash, $J_{1',2'}$=7.2 Hz), 4.09–4.16 (m, 2H, 3'-H and 4'-H), 3.96 (dd, 1H, 5'-H, $j_{4',5'}$=4.8 Hz, $J_{5'a,5'b}$=10.9 Hz), 3.86 (dd, 1H, 5'-H,$j_{4',5'}$=5.2 Hz, $J_{5'a,5'b}$=10.9 Hz). $^{13}$C-NMR (90.556 MHz, $d_6$-DMSO):δ 142.269, 140.958, 132.307, 126.214, 126.012, 120.351, 113.920, 89.198, 83.725, 70.972, 70.906, 33.769. Anal.Calcd. for $C_{12}H_{10}BrCl_3N_2O_3$: C, 34.61; H, 2.40; N, 6.73. Found: C, 34.75; H, 2.53; N, 6.40.

2,5,6-Trichloro-1-(5'-deoxy-5'-azido-β-D-ribofuranosyl) benzimidazole (17a)

Compound 16a (0.3 g, 6.5 mmol) was deprotected and recrystallized twice from MeOH to give 0.18 g (72%) of 17a as white crystals.

Mp: 150°–151° C. $R_f$ 0.42 (EtOAc/hexane 5/1 (v/v)). $^1$H-NMR (360 MHz, DMSO-$d_6$):δ 8.11 (s, 1H, $C_7$-H), 8.01 (s, 1H, $C_4$-H), 5.90 (d, 1H, 1'-H, $J_{1',2'}$=7.2 Hz), 5.64 (d, 1H, 2'-OH,$J_{2',2'-OJ}$=6.0 Hz, $D_2O$ exchangeable), 5.45 (d, 1H, 3'-OH, $J_{3',3'-OH}$=4.7 Hz, $D_2O$ exchangeable), 4.49 (q, 1H, 2'-H, collapses to a triplet on $D_2O$ wash, $J_{1',2'}$=7.0 Hz), 4.06 (m, 2H, 3'-H and 4'-H), 3.82 (m, 2H, 5'-H). $^{13}$C-NMR (90.556 MHz, $d_6$-DMSO):δ 142.203, 140.961, 132.360, 126.119, 125.959, 120.377, 113.910, 89.376, 83.280, 71.172, 69.751, 51.628. MS (EI 70 eV with DCI probe): Calcd. 376.9849, Found: 376.9821. IR 2096 $cm^{-1}$ (azide). Anal.Calcd. for $C_{12}H_{10}Cl_3N_5O_3$: C, 38.07; H, 2.66; N, 18.55. Found: C, 37.94; H, 2.53; N, 18.49.

2,5,6-Trichloro-1-(5'-deoxy-5'-methylthio-β-D-ribofuranosyl)benzimidazole (17b)

Compound 16b (0.3 g, 6.4 mmol) was deprotected as described before and recrystallized twice from MeOH to give 0.19 g (77%) of 17b as white crystals.

Mp: 111°–112° C. $R_f$ 0.63 (EtOAc/hexane 5/1(v/v)). $^1$H-NMR (360 MHz, DMSO-$d_6$):δ 8.05 (s, 1H, $C_7$-H), 8.00 (s, 1H, $C_4$-H), 5.88 (d, 1H, 1'-H, $J_{1',2'}$=7.3 Hz), 5.60 (m, 1H, 2'-OH, $D_2O$ exchangeable), 5.41 (m, 1H, 3'-OH, $D_2O$ exchangeable), 4.51 (m, 1H, 2'-H, collapses to a triplet on $D_2O$ wash, $J_{1',2'}$=7.0 Hz), 4.07 (m, 2H, 3'-H and 4'-H), 3.0 (dd, 1H, 5'-H, $j_{4',5'}$=5.8 Hz, $J_{5'a,5'b}$=13.9 Hz), 2.90 (dd, 1H, 5'-H, $j_{4',5'}$=5.8 Hz, $J_{5'a,5'b}$=13.9), 2.12 (s, 3H, $CH_3$S). $^{13}$C-NMR (90.556 MHz, $d_6$-DMSO):δ 142.195, 140.961, 132.341, 126.120, 125.921, 120.324, 113.839, 89.419, 84.157, 71.363, 71.147, 35.694, 15.819. Anal.Calcd. for $C_{13}H_{13}Cl_3N_2O_3S$: C, 40.70; H, 3.42; N, 7.30. Found: C, 40.49; H, 3.48; N, 7.09.

2,5,6-Trichloro-1-(2',3'-O-isopropylidene-β-D-ribofuranosvl)benzimidazole (18)

Compound 1 (2.5 g, 7 mmol) was suspended in dry acetone (30 mL). Dowex 50 ($H^+$) resin (0.5 g) and 2,2-dimethoxypropane (5 mL) were added and the reaction was stirred under argon atmosphere at room temperature for 2 h. The resin was removed by filtration and washed with acetone. The filtrate was evaporated under reduced pressure to give an oil. To this oil was added MeOH (20 mL). The desired product crystallized out of the MeOH-solution upon cooling. The product was collected by filtration and recrystallized from EtOH to give 2 g (73%) of 18 as white crystals.

Mp: 142°–143° C. $R_f$ 0.60 (EtOAc/hexane 1/1 (v/v)). $^1$H-NMR (300 MHz, DMSO-$d_6$):δ 8.32 (s, 1H, $C_7$-H), 7.98 (s, 1H, $C_4$-H), 6.08 (d, 1H, 1'-H, $J_{1',2'}$=4.2 Hz), 5.40 (t, 1H, 5'-OH), 5.07 (m, 1H, 2'-H), 5.01 (m, 1H, 3'-H), 4.18 (m, 1H, 4'-H), 3.74 (m, 2H, 5'-H) ,1.58 (s, 3H, $CH_3$), 1.32 (s, 3H, $CH_3$). Anal. Calcd. for $C_{15}H_{15}Cl_3N_2O_4$: C, 45.76; H, 3.84; N,7.12.Found:C,45.44;H,3.81;N,7.18.

2,5,6-Trichloro-1-(2',3'-O-isopylidene-5'-deoxy-5'-azido-β-D-ribofuransyl benzimidazole (19a)

Compound 18 (350 mg, 8.9 mmol) was dissolved in dry THF and triphenylphosphine (0.7 g, 29.4 mmol) was added to the reaction mixture. Diethyl azodicarboxylate (0.4 mL, 29.4 mmol) was added. The reaction mixture was stirred for 30 min, then diphenylphosphoryl azide (0.6 mL, 29.4 mmol) was added and the resulting mixture stirred at ambient temperature for 24 h under argon. The organic solvent was removed under reduced pressure and the remaining solid purified by flash chromatography (EtOAc/hexane 1/2 (v/v), 2 cm×15 cm). Fractions containing the nucleoside were contaminated with some aromatic impurity. These fractions were pooled and evaporated to dryness. A second chromatographic separation using chloroform as eluent ($CHCl_3$, 2 cm×15 cm) gave a clean nucleoside 18 as determined by TLC. Fractions containing 18 were combined, evaporated to dryness and recrystallized from MeOH to give 248 mg (71%) of 19a as white crystals.

Mp: 70°–72° C. $R_f$ 0.21 (EtOAc/hexane 1/2 (v/v)). $^1$H-NMR (300 MHz, DMSO-$d_6$):δ 8.11 (s, 1H, $C_7$-H), 8.00 (s, 1H, $C_4$-H), 6.15 (d, 1H, 1'-H, $J_{1',2'}$=4.4 Hz), 5.24 (q, 1H, 2'-H), 5.00 (q, 1H, 3'-H), 4.25 (m, 1H, 4'-H), 3.85 (m, 2H, 5'-H) ,1.58 (s, 3H, $CH_3$), 1.32 (s, 3H, $CH_3$). $^{13}$C-NMR (75.40 MHz, $d_6$-DMSO):δ 141.33, 140.87, 132.43, 126.54, 126.23, 120.34, 115.30, 113.57, 89.99, 82.11, 81.85, 79.91, 51.19, 26.89, 25.26. MS (DCI with $NH_3$) M/Z 418 (M+H). IR 2106 $cm^{-1}$ (azide). Anal. Calcd. for $C_{15}H_{14}Cl_3N_5O_3$* 1/2 MeOH: C, 42.83; H, 3.71; N, 16.11. Found: C, 43.15; H, 3.51; N, 16.07.

2,5,6-Trichloro-1-(5'-deoxy-5'-azido-β-D-riboflluranosyl) benzimidazole (17a)

Compound 19a (95 mg, 0.27 mmol) was dissolved in THF (10 mL) and 2N HCl (10 mL) was added to the solution. This reaction mixture was stirred for 6 h. Water (50 mL) was added to the reaction mixture, and the mixture was extracted with EtOAc (3×30 mL). The organic phase was washed successively with $NaHCO_3$ and with saturated NaCl solution, dried over sodium sulfate, decolorized with charcoal, filtered through Celite and concentrated under reduced pressure to give a solid. This solid was purified by flash chromatography (EtOAc, 2 cm×15 cm), fractions containing the nucleoside were pooled, concentrated to dryness and finally crystallized from EtOAc/hexane to give 60 mg (70%) of white crystals which were identical to 17a by TLC and $^1$H-NMR.

2,5,6-Trichloro-1-(2',3'-O-isopropylidene-5'-deoxy-5'-chloro-β-D-ribofuranosyl benzimidazole (19b)

Compound 18 (200 mg, 0.51 mmol) was dissolved in dry $CH_3CN$ and triphenylphosphine (263 mg, mmol) was added to the solution. $CCl_4$ (0.1 mL, 1 mmol) was then added to the reaction mixture and the mixture stirred at ambient temperature for 12 h under argon atmosphere. The organic solvent was removed under reduced pressure and the remaining solid purified by flash chromatography (EtOAc/hexane 1/2 (v/v), 2 cm×15 cm). Fractions containing the nucleoside were combined, evaporated to dryness and recrystallized from MeOH/$H_2O$ to give 100 mg (48%) of 19b as white crystals.

$R_f$ 0.60 (EtOAc/hexane 1/2 (v/v)). $^1$H-NMR (360 MHz, DMSO-$d_6$):δ 8.09 (s, 1H, $C_7$-H), 8.00 (s, 1H, $C_4$-H), 6.17 (d, 1H, 1'-H, $J_{1',2'}$=4.6 Hz), 5.23 (q, 1H, 2'-H, $J_{1',2'}$=4.6 Hz, $J_{2',3'}$=7.2 Hz), 5.02 (q, 1H, 3'-H, $J_{2',3'}$=7.2, Hz, $J_{3',4'}$=4.6), 4.35 (q, 1H, 4'-H, $J_{3',4'}$=4.6, $J_{4',5'}$=9.1 Hz), 4.01–4.08 (m, 2H, 5'-H) ,1.58 (s, 3H, $CH_3$), 1.32 (s, 3H, $CH_3$). $^{13}$C-NMR (90.556 MHz, $d_6$-DMSO):δ 141.325, 140.732, 132.288, 126.456, 126.172, 120.372, 115.441, 113.637, 89.683, 82.359, 81.629, 80.120, 43.975, 26.859, 25.228. Anal. Calcd. for $C_{15}H_{14}Cl_4N_2O_3$: C, 43.72; H, 3.42; N, 6.80. Found: C, 43.93; H, 3.31; N, 6.66.

2,5,6-Trichloro-1-(5'-deoxy-5'-chloro-β-D-ribofuranosyl) benzimidazole (13b)

Compound 19b (50 mg, 0.1 mmol) was deprotected and purified as described for 19a to give 20 mg (54%) of white crystals identical by TLC and $^1$H-NMR to 13b.

Antiviral Activity of Compounds

Cells and Viruses

KB cells (available from the American Type Culture Collection (ATCC) 12301 Parklawn Drive, Rockport, Md. 20852 (ATCC CCL 17)), an established human cell line derived from an epidermal oral carcinoma, were grown in minimal essential medium (MEM) (Sigma) with Hanks salts (MEM(H)) supplemented with 5% fetal calf serum. Human foreskin fibroblasts (HFF cells) (provided by the University of Michigan Hospital) and African green monkey kidney cells (BSC-1) (ATTC CCL 26) cells were grown in MEM with Earl salts (MEM(E)) supplemented with 10 % fetal bovine serum. Cells were passaged according to conventional procedures and as described in Shipman, C., Jr. et al. (1976) *Antimicrob. Agents Chemother.* Vol. 9:120 and incorporated herein by reference. Briefly, cells were passaged at 1:2 to 1:10 dilutions according to conventional procedures by using 0.05% trypsin plus 0.02% EDTA in a HEPES buffered salt solution. HFF cells were passaged only at 1:2 dilutions.

A plaque purified isolate, $P_0$, of the Towne strain of HCMV was used in all experiments and was a gift of Dr. Mark Stinski, University of Iowa. The KOS strain of HSV-1 was used and was provided by Dr. Sandra K. Weller, University of Connecticut. Stock preparations of HCMV and HSV-1 were prepared and titered as known to those of skill and the art and described in Turk, S. R. et al. (1987) *Antimicrob. Agents Chemother.* Vol. 31:544–550 and Shipman, C., Jr., etal. (1990) *J. Virol. Methods* Vol. 28:101–106, each incorporated herein by reference.

Briefly, high titer HSV-I stocks were prepared as follows. Nearly confluent monolayer cultures of KB cells were grown in 32 oz. glass bottles containing MEM(E) buffered with 25 mM HEPES and supplemented with 5% fetal bovine serum and 0.127 g/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min.). The resulting virus pools were stored at −76° C. until retrieved for use in experiments.

HSV-I was titered using monolayer cultures of BSC-1 cells. Cells were planted at 3×10$^5$ cells/well using 6-well cluster dishes. MEM(E) supplemented with 10% fetal bovine serum was employed as medium. After 22–24 h, cells were 90% confluent and were inoculated in triplicate using at least three ten-fold dilutions with 0.2 mL of the virus suspension to be assayed and incubated in a humidified 4% $CO_2$-90% air atmosphere for one hour to permit viral adsorption. Following virus adsorption, the cell sheet was overlayed with 5 mL of MEM(E) with 5% serum plus 0.5% methocel (4000 CPS) and incubated an additional two to three days. Cells were fixed and stained with 0. 1% crystal violet in 20% methanol and macroscopic plaques enumerated.

Stock HCMV was prepared by infecting HFF cells at a multiplicity of infection (m.o.i.) of less that 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HCMV was titered in 24-well cluster dishes which were plated to contain 5×10$^4$ HFF cells/well, grown as described above. When the cells were 70 to 80% confluent, 0.2 mL of the virus suspension was added per well and adsorbed as described above. At least three ten-fold dilutions of each preparation were used. Following virus adsorption, the cell sheets were overlayed with 0.5% methocel (4000 CPS) in maintenance medium (MEM(E) with 1.1 g/liter NaHCO$_3$, 100 units/mL penicillin G, 100 μg/mL streptomycin, and 5% fetal bovine serum). The cultures were incubated in a humidified atmosphere of 4% $CO_2$-96% air. Viral plaques were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

Assays for Antiviral Activity

HCMV plaque reduction experiments were performed with monolayer cultures of HFF cells by a procedure similar to that referenced above for titration of the viruses and described in Devivar, R. V. et al. (1994) *J. Med. Chem.* Vol. 37:2942–2949. Activity of compounds against HSV-1 was evaluated using an ELISA assay.

HSV-1

ELISA techniques according to standard procedures were also used to determine activity against HSV- 1. Drug effects were calculated as a percentage of the reduction in virus titers in the presence of each drug concentration compared to the titer obtained in the absence of drug. Ganciclovir was used as a positive control in all experiments.

HCMV

The effect of compounds of the replication of HCMV was measured using a plaque (focus) reduction assay. For the former, HFF cells in 24-well culture dishes were infected with approximately 50 p.f.u. of HCMV per well using the procedures detailed above. Compounds dissolved in growth medium were added in four to six selected concentrations to duplicate wells following virus adsorption. Following incubation at 37° C. for 7 to 10 days, cell sheets were fixed, stained and microscopic plaques were enumerated as described above. Drug effects were calculated as a percentage of reduction in number of plaques in the presence of each drug concentration compared to the number observed in the absence of drug. DHPG (ganciclovir) was used as a positive control in all experiments.

Assays for Cytotoxicity

Two different methods were used to evaluate cytotoxicity of the compounds. First, cytotoxicity produced in stationary HFF cells was determined by microscopical examination of cells not affected by the virus used in the plaque assay. Second the effect of compounds on KB cells during two population doubling times was determined by crystal violet staining and spectrophotometric quantitation of dye eluted from stained cells. This method has been utilized for the analysis of ganciclovir and zidovudine (See Prichard, M. N. et al. *Antiviral Res.* (1991) Vol. 35:1060–1065).

In Vitro Antiproliferative Activity

Antiproliferative activity was evaluated by measuring the effect of the compounds on the growth of L1210 cells, a mouse leukemia cell line which is generally available and can be obtained from Cancer Chemotherapy Center, Japanese Foundation for Cancer Research. Antiproliferative activity was measured using conventional procedures and as described in Wotring, L. L. and Townsend, L. B., (1979) *Cancer Res.* Vol. 39:3018–3023 and Cory, A. H. et al. (1991) *Cancer Comm.* Vol. 3:207–212, each incorporated herein by reference.

Data Analysis

Dose-response relationships can be used to compare drug effects. These are constructed by linearly regressing the percent inhibition of parameters derived in the preceding sections against log drug concentrations. The 50 inhibitory ($I_{50}$) concentrations were calculated from the regression lines using the methods described by Goldstein. See Goldstein, A., *Biostatistics: An Introductory Text,* MacMillan, New York, pp. 156–161 (1964), incorporated herein by reference.

Drug Combination and Synergy

The compounds of the invention, could thus be used to treat HCMV infections in AIDS patients already receiving the antiviral drug zidovudine (AZT). Combination therapies with AZT provides the advantage of less toxicity over the combination of ganciclovir with AZT. The combination of the compounds of this invention with AZT likely produces less cytotoxicity (i.e. antagonism) in cultured human cells than either agent used alone. In contrast, combination of ganciclovir with AZT produces greater cytotoxicity in human cells than the use of either of these drugs alone.

Analysis

For all the compounds in Table 1, the acetylated derivatives and the deprotected derivatives had identical activity. Either the acetyls are removed in vitro or the benzimidazole nucleoside binding site tolerates substitutions on the 2' and 3'-hydroxyls. The fact that the isopropylidene derivatives 18 and 19a–b have significantly less activity than the corresponding deprotected derivatives (1, 17a and 13b) would indicate that the first assumption is correct.

The 5'-O-alkyl benzimidazole nucleosides (7a–7d and 8a–8c) all have good anti-HCMV activity, many of them with activity similar to TCRB (1). The activity decreases slightly with an increased size of the alkyl group from methyl (8a) to butyl (9c). The increase in the length of the alkyl chain to a hexyl (7d) gave decreased activity over the butyl compound (7c). Substitution of the 5'-oxygen with sulfur did not affect activity as the methylthio derivative (17b) was shown to be equally active as the 5'-O-ethyl derivative (8b). The 5'-O-alkyl benzimidazole nucleosides (7a–7d and 8a–8c) and the methylthio derivative (17b) were more cytotoxic than TCRB (1). Their selectivity index was lower than that of TCRB (1).

The 5'-halogenated derivatives (12a-d and 13-c) also had very good anti-HCMV activity. There was little difference between the different 5'-halogenated derivatives, indicating that the electronegativity of the 5'-substituent does not have a major effect on the activity of benzimidazole nucleosides. These derivatives were more cytotoxic than TCRB (1) in the HFF cell assay. In growing KB cells, the compounds were less cytotoxic. In particular, compounds 12a and 13a exhibited little or no cytoxicity thereby establishing that activity against HCMV is a specific antiviral effect. Likewise, compound 13a had no antiproliferative effect in L1210 cells (see Table 2) further illustrating its lack of cytotoxicity.

The azido derivative (17a) had similar anti-HCMV activity as TCRB, but may be more cytotoxic.

None of the compounds of this invention had any significant activity against HSV-1. This is not surprising in view of the established selective action of other benzimidazole nucleosides only against HCMV. The compounds furthermore had little antiproliferative activity against HSV-1 (Table 2).

The embodiments of this invention illustrated above are intended to aid in an understanding of the invention but are not intended to, and should not be construed to, limit in any way the invention as set forth in the following claims. Other aspects, advantages and modifications within the scope of this invention will be apparent to those skilled in the art to which this invention pertains.

TABLE 1

Antiviral Activity and Cytotoxicity of 5'-Substituted-Ribofuranosyl-2,5,6-Trichlorobenzimidazole Nucleosides

|  | Substituents |  | 50% Inhibitory Concentration ($\mu$M)(1) | | | |
|---|---|---|---|---|---|---|
|  |  |  | Antiviral Activity (2) | | Cytotoxicity (3) | |
| Compound | $R_2, R_3$ | R | (plaque) | (ELISA) | (HFF) | (KB) |
| 7a | OAc | OCH$_3$ | 2.8 | >100 | 26 | 80 |
| 7b | OAc | OEt | 4.3 | >100 | 33 | 60 |
| 7c | OAc | OBu | 21 | >100 | 66 | >100 |
| 7d | OAc | OHex | 8 | >100 | 32 | 60 |
| 8a | OH | OCH$_3$ | 3 | >100 | 26 | 90 |
| 8b | OH | OEt | 4.6 | >100 | 26 | 80 |
| 8c | OH | OBu | 14.2 | >100 | 32 | 60 |
| 8d | OH | OHex | ND (4) | ND | ND | ND |
| 12a | OAc | F | 0.6 | >100 | 32 | 100 |
| 12b | OAc | Cl | 1.4 | >100 | 32 | 90 |
| 12c | OAc | Br | 2.7 | >100 | 32 | 60 |
| 12d | OAc | I | 2.5 | >100 | 32 | 60 |
| 13a | OH | F | 0.5 | >100 | 32 | >100 |

TABLE 1-continued

Antiviral Activity and Cytotoxicity of 5'-Substituted-Ribofuranosyl-2,5,6-Trichlorobenzimidazole Nucleosides

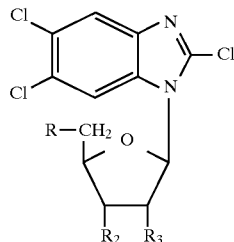

| | Substituents | | 50% Inhibitory Concentration ($\mu$M)(1) | | | |
| | | | Antiviral Activity (2) | | Cytotoxicity (3) | |
| Compound | $R_2$, $R_3$ | R | (plaque) | (ELISA) | (HFF) | (KB) |
|---|---|---|---|---|---|---|
| 13b | OH | Cl | 1.0 | >100 | 32 | 90 |
| 13c | OH | Br | 1.5 | >100 | 32 | 90 |
| 13d | OH | I | 3.2 | ND | 32 | ND |
| 16a | OAc | $N_3$ | 1.5 | >100 | 32 | 70 |
| 16b | OAc | $SCH_3$ | 4.8 | >100 | 32 | >100 |
| 17a | OH | $N_3$ | 1.5 | >100 | 32 | 70 |
| 17b | OH | $SCH_3$ | 4.5 | >100 | 32 | >100 |
| 18 | —O-i-Pr—O— (5) | H | 12.4 | ND | >100 | ND |
| 19a | —O-i-Pr—O— | $N_3$ | 10.9 | ND | 32 | ND |
| 19b | —O-i-Pr—O— | Cl | 13.5 | >100 | 66 | 100 |
| 1 | OH | OH | 2.76 | >100 | 238 | 210 |
| 2 | OH | H | 0.36 | >100 | 77 | 150 |
| DHPG | NA(6) | NA | 7.4(7) | 3.5 | >100 | >100 |

(1) All values are averages from two or more experiments. Values > 100 $\mu$M (or > 10) indicate that $IC_{50}$ was not reached at highest concentration tested (or highest concentration at which the compound was soluble).
(2) A plaque assay was used to quantitate anti HCMV activity, an ELISA assay was used to quantitate activity against HSV-1. DHPG (ganciclovir) was used as a positive control for the HMCV assay.
(3) Visual cytotoxicity was scored on HFF cells at the time of HCMV plaque enumeration. Inhibition of KB cell growth was determined as described in the experimental. 3L was used as a positive control for the KB cytotoxicity assay.
(4) ND: Not determined.
(5) —O-i-Pr—O—: 2',3'-O-isopropylidene ($R_2$ and $R_3$ together are —O—CH($CH_3$)$_2$—O—).
(6) NA: Not Applicable.
(7) This value 2.6 (+/−0.4) $\mu$M is the average for the 5 experiments used to determine the $IC_{50}$ values reported in the table.

TABLE 2

Antiproliferative Activity of 5'-Substituted-Ribofuranosyl-2,5,6-Trichlorobenzimidazole Nucleosides

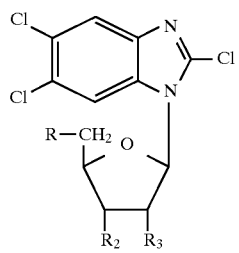

| | Substituents | | 50% Inhibitory Concentration ($\mu$M) (8) |
| Compound | $R_2$, $R_3$ | R | Antiproliferative Activity |
|---|---|---|---|
| 7a | OAc | $OCH_3$ | ND |
| 7b | OAc | OEt | ND |
| 7c | OAc | OBu | ND |
| 7d | OAc | OHex | ND |

TABLE 2-continued

Antiproliferative Activity of 5'-Substituted-Ribofuranosyl-2,5,6-Trichlorobenzimidazole Nucleosides

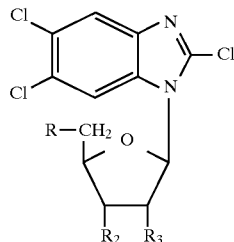

| Compound | Substituents $R_2, R_3$ | R | 50% Inhibitory Concentration ($\mu$M) (8) Antiproliferative Activity |
|---|---|---|---|
| 8a | OH | OCH$_3$ | 60 |
| 8b | OH | OEt | 59 |
| 8c | OH | OBu | >100 |
| 8d | OH | OHex | ND |
| 12a | OAc | F | ND |
| 12b | OAc | Cl | ND |
| 12c | OAc | Br | ND |
| 12d | OAc | I | ND |
| 13a | OH | F | >100 |
| 13b | OH | Cl | >100 |
| 13c | OH | Br | 100 |
| 13d | OH | I | ND |
| 16a | OAc | N$_3$ | ND |
| 16b | OAc | SCH$_3$ | ND |
| 17a | OH | N$_3$ | 80 |
| 17b | OH | SCH$_3$ | >100 |
| 18 | —O-i-Pr—O— | H | ND |
| 19a | —O-i-Pr—O— | N$_3$ | ND |
| 19b | —O-i-Pr—O— | Cl | ND |

(8) The concentration required to decrease the final growth rate of L1210 cells to half of the control rate. All values are averages from two or more experiments.

All publications, patents, and patent applications cited in this specification are herein incorporated by reference as if each individual publication, patent, or patent application were specifically and individually indicated to be incorporated by reference.

We claim:

1. A compound of the formula:

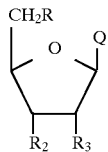

wherein

Q is a substituted benzimidazole group attached at the benzimidazole 1-position which substituted benzimidazole group comprises a 2-substituent which is other than —H;

R is —F, —Cl, —Br, —I, —N$_3$, or —X—R$_1$, wherein X is —O— or —S— and R$_1$ is a straight or branched chain alkyl of 1 to 8 carbon atoms; and R$_2$ is —O—C(=O)CH$_3$ or —OH;

R$_3$ is —O—C(=O)CH$_3$ or —OH;

or an α-L, α-D, or β-L analog thereof:

or a pharmaceutically acceptable salt thereof.

2. The compound of claim 1, wherein R is —F.

3. The compound of claim 1, wherein R is —Cl.

4. The compound of claim 1, wherein R is —Br.

5. The compound of claim 1, wherein R is —I.

6. The compound of claim 1, wherein R is —N$_3$.

7. The compound of claim 1, wherein R is —X—R$_1$, wherein X is —O— and R$_1$ is a straight or branched chain alkyl of 1 to 8 carbon atoms.

8. The compound of claim 1, wherein R is —O—CH$_3$.

9. The compound of claim 1, wherein R is —O—CH$_2$CH$_3$.

10. The compound of claim 1, wherein R is —O—CH$_2$CH$_2$CH$_2$CH$_3$.

11. The compound of claim 1, wherein R is —O—CH$_2$CH$_2$CH$_2$CH$_2$CH$_2$CH$_3$.

12. The compound of claim 1, wherein R is —X—R$_1$, wherein X is —S— and R$_1$ is a straight or branched chain alkyl of 1 to 8 carbon atoms.

13. The compound of claim 1, wherein R is —S—CH$_3$.

14. A compound of the formula:

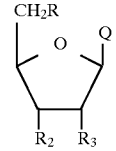

wherein

Q is a substituted benzimidazole group attached at the benzimidazole 1-position and is selected from the group consisting of:

2,5,6-trichlorobenzimidazole,
2-bromo-5,6-dichlorobenzimidazole,
2,4,6-trichlorobenzimidazole,
2-bromo-4,6-dichlorobenzimidazole,
2,4,5,6-tetrachlorobenzimidazole,
2-bromo-4,5,6-trichlorobenzimidazole,
2-amino-4,5-dichlorobenzimidazole,
2-isopropylamino-4,5-dichlorobenzimidazole,
2-methoxy-4,5-dichlorobenzimidazole, and
2-trifluoromethyl-4,5-dichlorobenzimidazole;

R is —F, —Cl, —Br, —I, —$N_3$, or —X—$R_1$, wherein X is —O— or —S— and $R_1$ is a straight or branched chain alkyl of 1 to 8 carbon atoms; and $R_2$ is —O—C(=O)$CH_3$ or —OH;
$R_3$ is —O—C(=O)$CH_3$ or —OH;
or an α-L, α-D, or β-L analog thereof;
or a pharmaceutically acceptable salt thereof.

15. The compound of claim 14, wherein R is —F.
16. The compound of claim 14, wherein R is —Cl.
17. The compound of claim 14, wherein R is —Br.
18. The compound of claim 14, wherein R is —I.
19. The compound of claim 14, wherein R is —$N_3$.
20. The compound of claim 14, wherein R is —X—$R_1$, wherein X is —O— and $R_1$ is a straight or branched chain alkyl of 1 to 8 carbon atoms.
21. The compound of claim 14, wherein R is —O—$CH_3$.
22. The compound of claim 14, wherein R is —O—$CH_2CH_3$.
23. The compound of claim 14, wherein R is —O—$CH_2CH_2CH_2CH_3$.
24. The compound of claim 14, wherein R is —O—$CH_2CH_2CH_2CH_2CH_2CH_3$.
25. The compound of claim 14, wherein R is —X—$R_1$, wherein X is —S— and $R_1$ is a straight or branched chain alkyl of 1 to 8 carbon atoms.
26. The compound of claim 14, wherein R is —S—$CH_3$.
27. A compound of the formula:

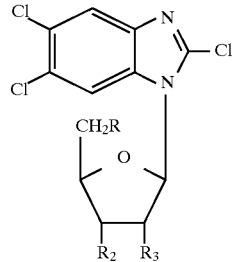

wherein
R is —F, —Cl, —Br, —I, —$N_3$, or —X—$R_1$, wherein X is —O— or —S— and $R_1$ is a straight or branched chain alkyl of 1 to 8 carbon atoms; and $R_2$ is —O—C(=O)$CH_3$ or —OH;
$R_3$ is —O—C(=O)$CH_3$ or —OH;
or an α-L, α-D, or β-L analog thereof;
or a pharmaceutically acceptable salt thereof.

28. The compound of claim 27, wherein R is —F.
29. The compound of claim 27, wherein R is —Cl.
30. The compound of claim 27, wherein R is —Br.
31. The compound of claim 27, wherein R is —I.
32. The compound of claim 27, wherein R is —$N_3$.
33. The compound of claim 27, wherein R is —X—$R_1$, wherein X is —O— and $R_1$ is a straight or branched chain alkyl of 1 to 8 carbon atoms.

34. The compound of claim 27, wherein R is —O—$CH_3$.
35. The compound of claim 27, wherein R is —O—$CH_2CH_3$.
36. The compound of claim 27, wherein R is —O—$CH_2CH_2CH_2CH_3$.
37. The compound of claim 27, wherein R is —O—$CH_2CH_2CH_2CH_2CH_2CH_3$.
38. The compound of claim 27, wherein R is —X—$R_1$, wherein X is —S— and $R_1$ is a straight or branched chain alkyl of 1 to 8 carbon atoms.
39. The compound of claim 27, wherein R is —S—$CH_3$.
40. A compound of the formula:

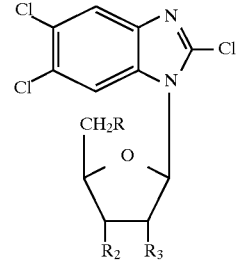

wherein
R is —F, —Cl, —Br, —I, —$N_3$, or —X—$R_1$, wherein X is —O— or —S— and $R_1$ is a straight or branched chain alkyl of 1 to 8 carbon atoms; and $R_2$ is —O—C(=O)$CH_3$ or —OH;
$R_3$ is —O—C(=O)$CH_3$ or —OH;
or a pharmaceutically acceptable salt thereof.

41. The compound of claim 40, wherein R is —F.
42. The compound of claim 40, wherein R is —Cl.
43. The compound of claim 40, wherein R is —Br.
44. The compound of claim 40, wherein R is —I.
45. The compound of claim 40, wherein R is —$N_3$.
46. The compound of claim 40, wherein R is —X—$R_1$, wherein X is —O— and $R_1$ is a straight or branched chain alkyl of 1 to 8 carbon atoms.
47. The compound of claim 40, wherein R is —O—$CH_3$.
48. The compound of claim 40, wherein R is —O—$CH_2CH_3$.
49. The compound of claim 40, wherein R is —O—$CH_2CH_2CH_2CH_3$.
50. The compound of claim 40, wherein R is —O—$CH_2CH_2CH_2CH_2CH_2CH_3$.
51. The compound of claim 40, wherein R is —X—$R_1$, wherein X is —S— and $R_1$ is a straight or branched chain alkyl of 1 to 8 carbon atoms.
52. The compound of claim 40, wherein R is —S—$CH_3$.
53. A composition comprising a compound according to claim 1, and a pharmaceutically acceptable carrier.
54. A composition comprising a compound according to claim 14, and a pharmaceutically acceptable carrier.
55. A composition comprising a compound according to claim 27, and a pharmaceutically acceptable carrier.
56. A composition comprising a compound according to claim 40, and a pharmaceutically acceptable carrier.
57. A method of inhibiting viral proliferation in a virally infected cell comprising contacting the cell with an effective amount of a compound according to claim 1 under suitable conditions such that viral proliferation is inhibited.
58. A method of inhibiting HCMV proliferation in a IICMV infected cell comprising contacting the cell with an effective amount of a compound according to claim 1 under suitable conditions such that HCMV proliferation is inhibited.

59. A method of inhibiting viral proliferation in a virally infected cell comprising contacting the cell with an effective amount of a compound according to claim 14 under suitable conditions such that viral proliferation is inhibited.

60. A method of inhibiting HCMV proliferation in a HCMV infected cell comprising contacting the cell with an effective amount of a compound according to claim 14 under suitable conditions such that HCMV proliferation is inhibited.

61. A method of inhibiting viral proliferation in a virally infected cell comprising contacting the cell with an effective amount of a compound according to claim 27 under suitable conditions such that viral proliferation is inhibited.

62. A method of inhibiting HCMV proliferation in a HCMV infected cell comprising contacting the cell with an effective amount of a compound according to claim 27 under suitable conditions such that HCMV proliferation is inhibited.

63. A method of inhibiting viral proliferation in a virally infected cell comprising contacting the cell with an effective amount of a compound according to claim 40 under suitable conditions such that viral proliferation is inhibited.

64. A method of inhibiting HCMV proliferation in a HCMV infected cell comprising contacting the cell with an effective amount of a compound according to claim 40 under suitable conditions such that HCMV proliferation is inhibited.

* * * * *

UNITED STATES PATENT AND TRADEMARK OFFICE
CERTIFICATE OF CORRECTION

PATENT NO. : 5,874,413
DATED : February 23, 1999
INVENTOR(S) : L. Townsend *et al.*

It is certified that error appears in the above-indentified patent and that said Letters Patent is hereby corrected as shown below:

In the drawings, Sheet 1, Fig. 1, the left-hand structure should appear as follows:

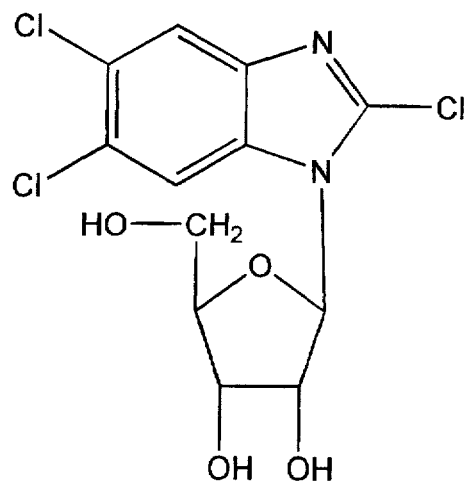

1

TCRB

UNITED STATES PATENT AND TRADEMARK OFFICE
CERTIFICATE OF CORRECTION

PATENT NO. : 5,874,413
DATED : February 23, 1999
INVENTOR(S) : L. Townsend et al.

It is certified that error appears in the above-indentified patent and that said Letters Patent is hereby corrected as shown below:

In the drawings, Sheet 1, Fig. 1, the right-hand structure should appear as follows:

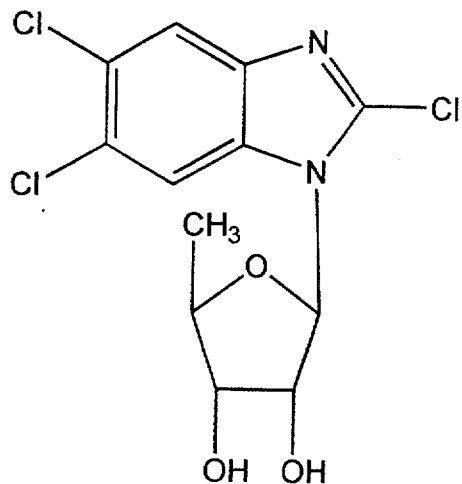

2

5'-deoxy-TCRB

UNITED STATES PATENT AND TRADEMARK OFFICE
CERTIFICATE OF CORRECTION

PATENT NO. : 5,874,413
DATED : February 23, 1999
INVENTOR(S) : L. Townsend *et al.*

Figure 2:
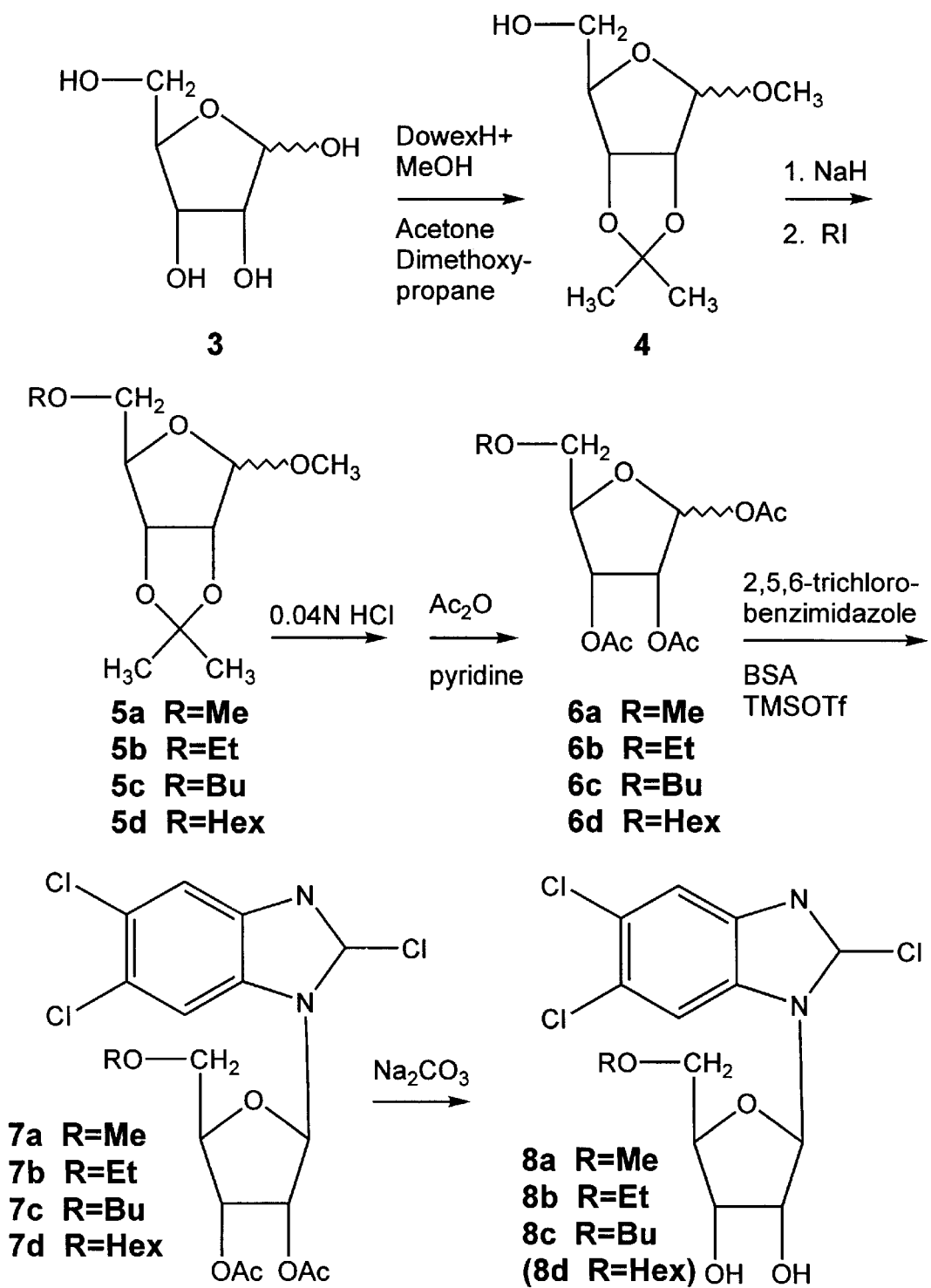
FIG. 2 is a schematic of the syntheses of a number of 2,5,6-trichloro-1-(5'-O-alkyl-β-D-ribofuranosyl) benzimidazoles (Scheme 2).

It is certified that error appears in the above-indentified patent and that said Letters Patent is hereby corrected as shown below:

In the drawings, Sheet 2, Fig. 2, the bottom reaction should appear as follows:

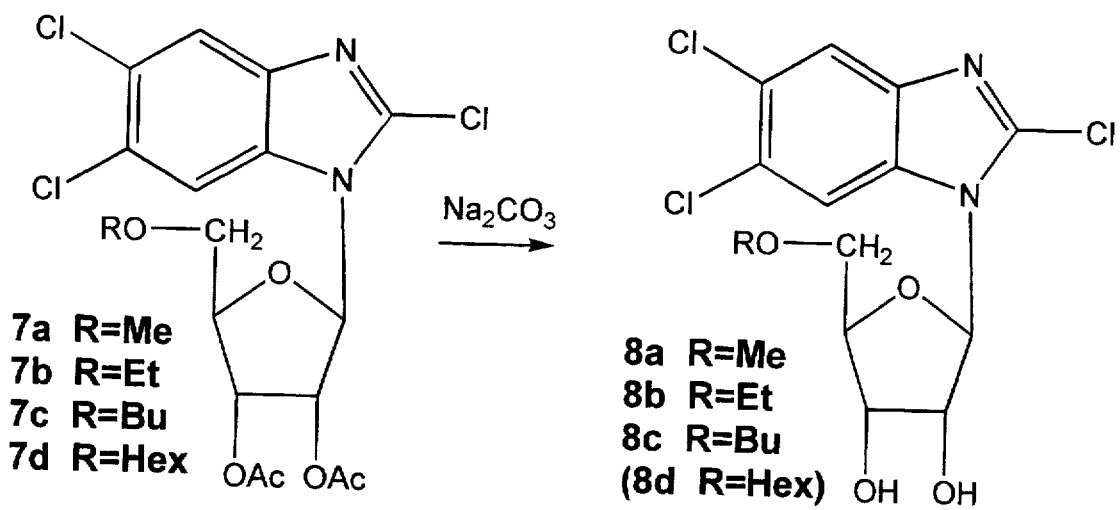

UNITED STATES PATENT AND TRADEMARK OFFICE
CERTIFICATE OF CORRECTION

PATENT NO. : 5,874,413
DATED : February 23, 1999
INVENTOR(S) : L. Townsend *et al.*

Figure 3:
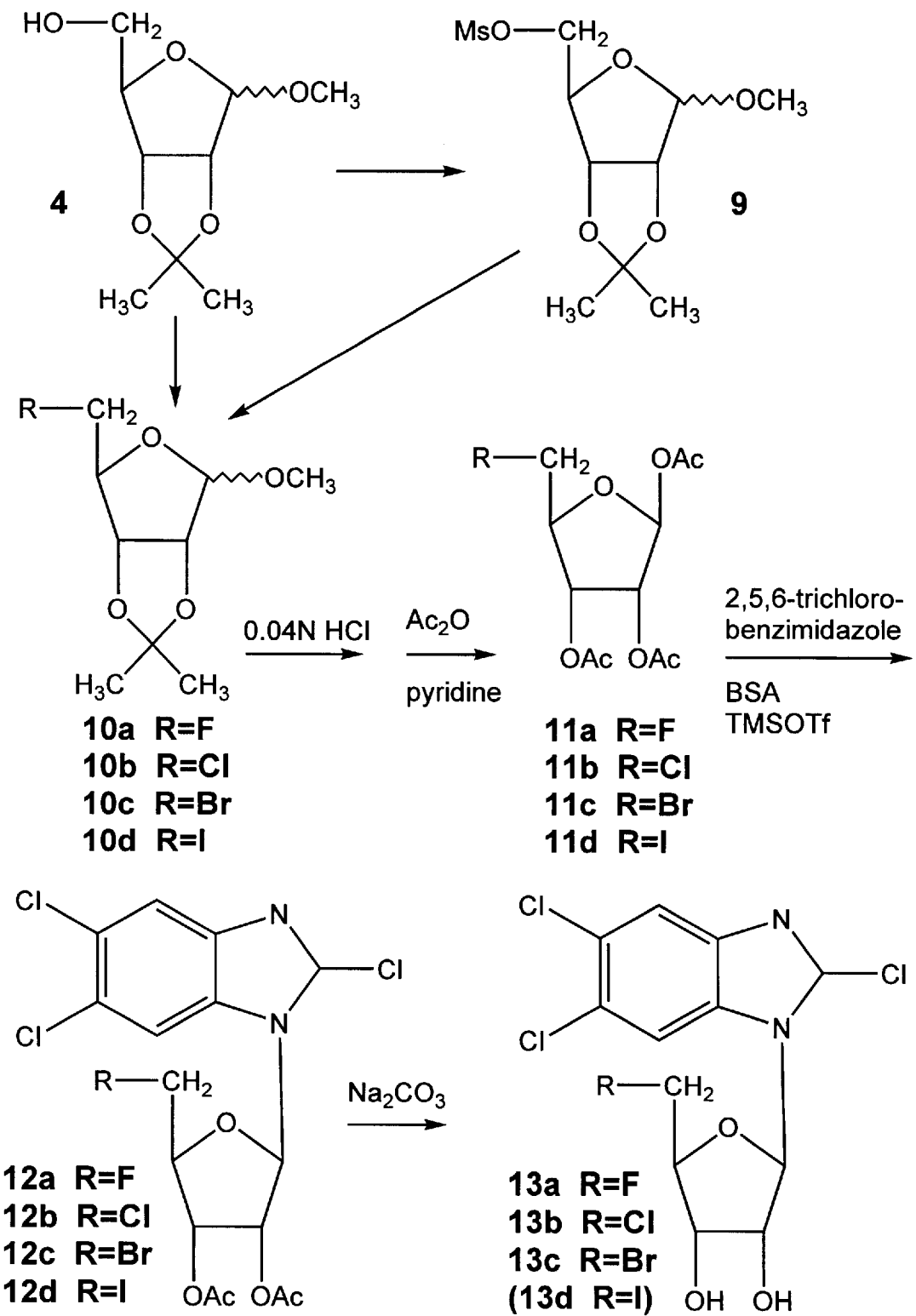
FIG. 3 is a schematic of the syntheses of a number of 2,5,6-trichloro- 1-(5'-deoxy-5'-halo-β-D-ribofuranosyl) benzimidazoles (Scheme 3).

It is certified that error appears in the above-indentified patent and that said Letters Patent is hereby corrected as shown below:

In the drawings, Sheet 3, Fig. 3, the bottom reaction should appear as follows:

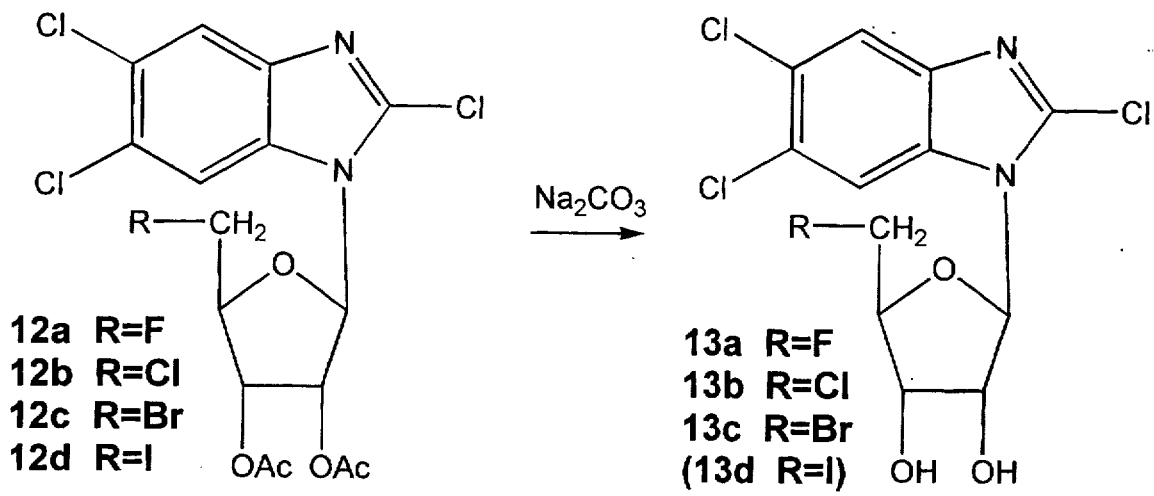

UNITED STATES PATENT AND TRADEMARK OFFICE
CERTIFICATE OF CORRECTION

PATENT NO. : 5,874,413
DATED : February 23, 1999
INVENTOR(S) : L. Townsend et al.

Figure 4:
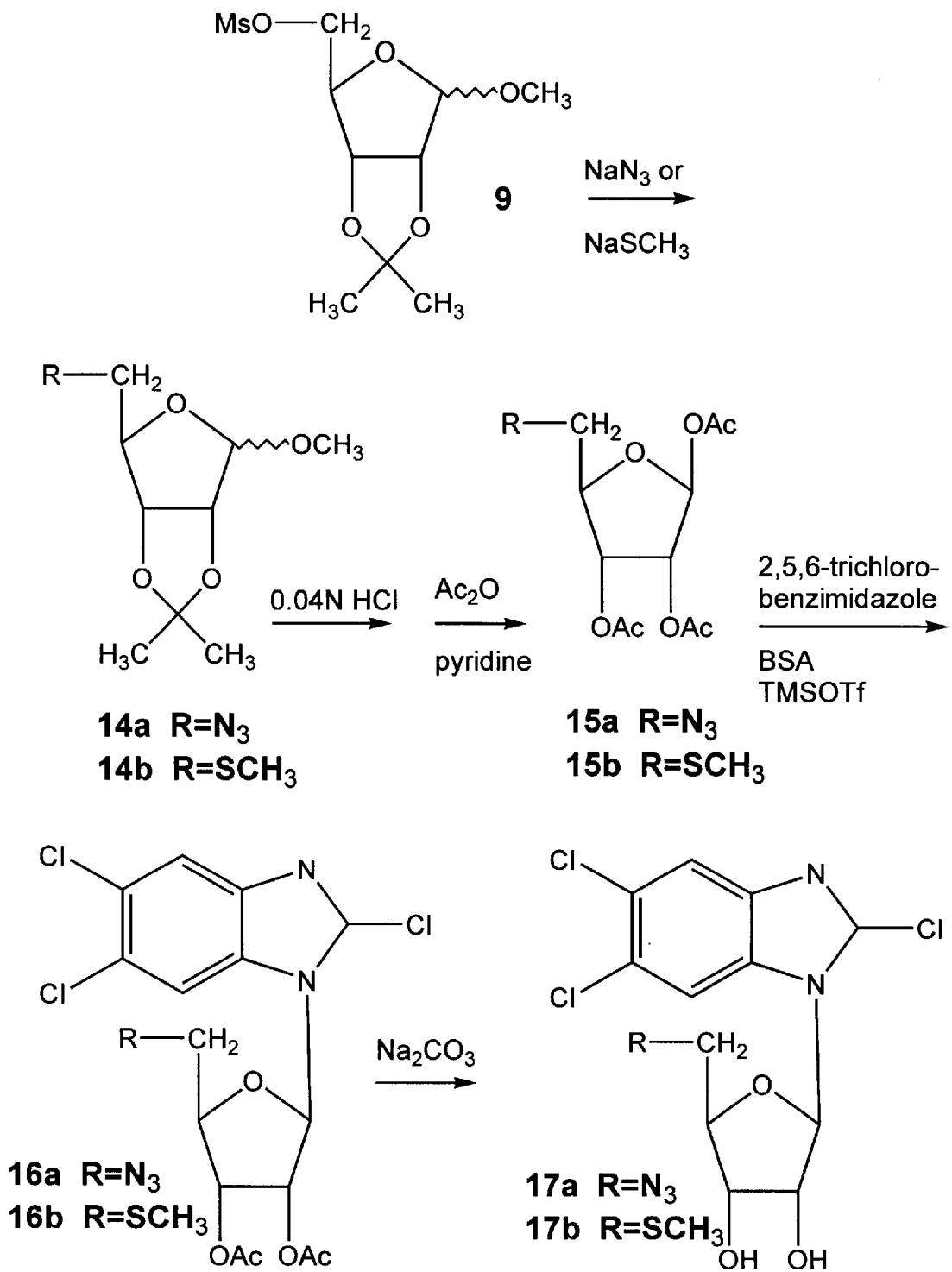
FIG. 4 is a schematic of the syntheses of a number of 2,5,6-trichloro-1-(5'-deoxy-5'-methylthio-β-D-ribofuranosyl)benzimidazoles and 2,5,6-trichloro- 1-(5'-deoxy-5'-azido-β-D-ribofuranosyl)benzimidazoles(Scheme 4).

It is certified that error appears in the above-indentified patent and that said Letters Patent is hereby corrected as shown below:

In the drawings, Sheet 4, Fig. 4, the bottom reaction should appear as follows:

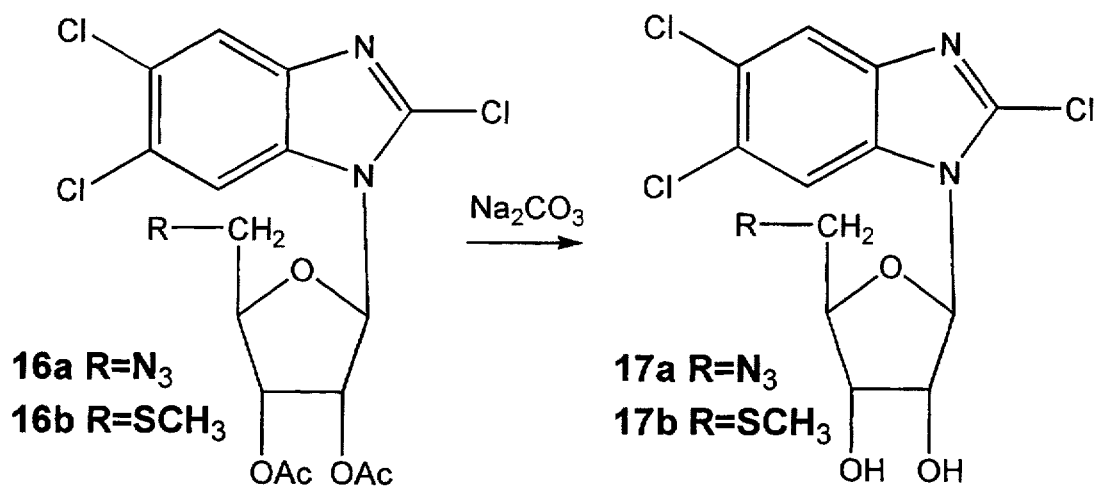

UNITED STATES PATENT AND TRADEMARK OFFICE
CERTIFICATE OF CORRECTION

PATENT NO. : 5,874,413

DATED : February 23, 1999

INVENTOR(S) : L. Townsend *et al.*

It is certified that error appears in the above-indentified patent and that said Letters Patent is hereby corrected as shown below:

In the drawings, Sheet 5, Fig. 5, the bottom reaction should appear as follows:

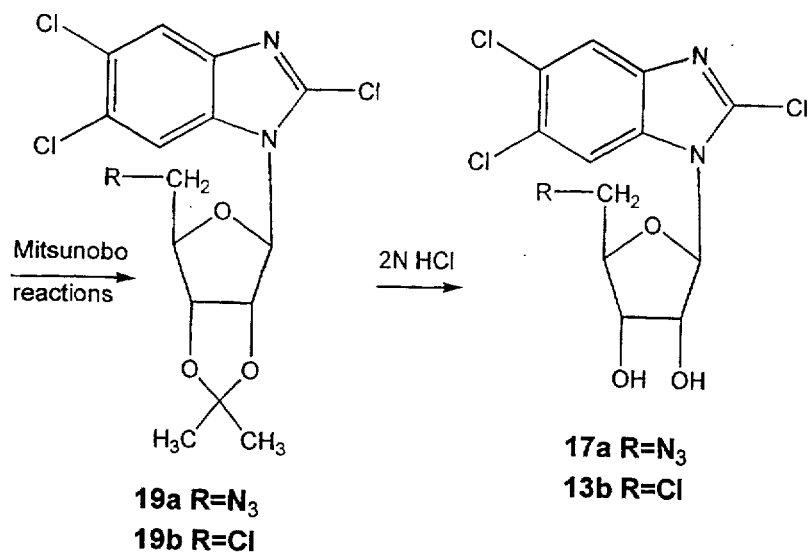

Signed and Sealed this

Twenty-third Day of November, 1999

Attest:

Q. TODD DICKINSON

Attesting Officer      Acting Commissioner of Patents and Trademarks

UNITED STATES PATENT AND TRADEMARK OFFICE
CERTIFICATE OF CORRECTION

PATENT NO. : 5,874,413
DATED : February 23, 1999
INVENTOR(S) : Leroy B. Townsend, et al.

It is certified that error appears in the above-identified patent and that said Letters Patent is hereby corrected as shown below:

In the drawings, Sheet 5, Fig. 5, the top reaction should appear as follows:

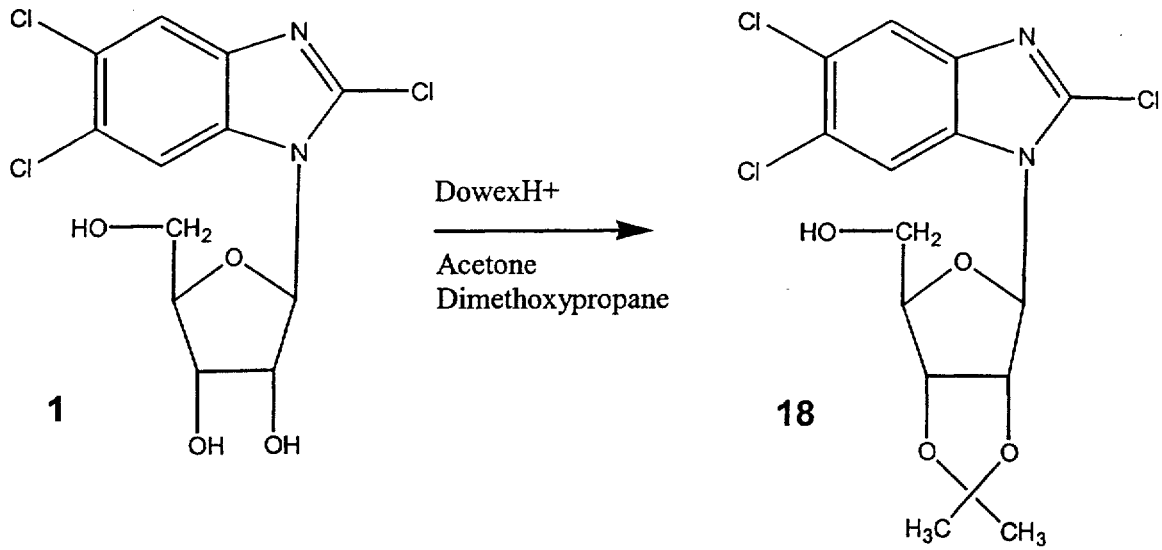

Signed and Sealed this

Eighth Day of August, 2000

Attest:

Q. TODD DICKINSON

Attesting Officer

Director of Patents and Trademarks